(12) United States Patent
Lineaweaver

(10) Patent No.: US 10,123,725 B2
(45) Date of Patent: Nov. 13, 2018

(54) HEARING PROSTHESIS EFFICACY ALTERING AND/OR FORECASTING TECHNIQUES

(71) Applicant: Cochlear Limited, Macquarie University, NSW (AU)

(72) Inventor: Sean Lineaweaver, Gig Harbor, WA (US)

(73) Assignee: Cochlear Limited, Macquarie University, NSW (AU)

(*) Notice: Subject to any disclaimer, the term of this patent is extended or adjusted under 35 U.S.C. 154(b) by 25 days.

(21) Appl. No.: 14/940,606

(22) Filed: Nov. 13, 2015

(65) Prior Publication Data

US 2016/0140873 A1    May 19, 2016

Related U.S. Application Data

(60) Provisional application No. 62/081,165, filed on Nov. 18, 2014.

(51) Int. Cl.
*A61B 5/12* (2006.01)
*H04R 25/00* (2006.01)
*G09B 21/00* (2006.01)

(52) U.S. Cl.
CPC ............ *A61B 5/123* (2013.01); *G09B 21/009* (2013.01); *H04R 25/70* (2013.01)

(58) Field of Classification Search
CPC ....... A61B 5/121; A61B 5/4851; A61B 5/123; H04R 25/70
See application file for complete search history.

(56) References Cited

U.S. PATENT DOCUMENTS

| 5,923,764 | A  | * | 7/1999 | Shennib ................ A61B 5/121 |
| | | | | 381/23.1 |
| 7,043,303 | B1 | * | 5/2006 | Overstreet ......... A61N 1/36036 |
| | | | | 607/57 |
| 8,533,001 | B2 | | 9/2013 | Skiba |
| 8,568,145 | B2 | | 10/2013 | Jastrzembski et al. |
| 9,592,382 | B2 | * | 3/2017 | Kulkarni ............ A61N 1/36032 |
| 2005/0027537 | A1 | * | 2/2005 | Krause .................... G10L 25/00 |
| | | | | 704/271 |

(Continued)

FOREIGN PATENT DOCUMENTS

KR      1020140081430 A    7/2014
WO      2005/002431 A1    1/2005

OTHER PUBLICATIONS

International Search Report and Written Opinion for PCT/IB2015/058797, dated Feb. 23, 2016.

*Primary Examiner* — Matthew Eason
(74) *Attorney, Agent, or Firm* — Pilloff & Passino LLP; Martin J. Cosenza

(57) ABSTRACT

A method of forecasting subjective efficacy of a hearing prosthesis implanted in a recipient, including subjecting a recipient to a plurality of temporally spaced aural training tasks, the aural training tasks evoking hearing percepts with the hearing prosthesis, obtaining first data indicative of the recipient's ability to hear with the hearing prosthesis based on performance by the recipient of the temporally spaced aural training tasks, and forecasting second data based on the first data, wherein the second data are indicative of the recipient's ability to hear with the hearing prosthesis at one or more temporal locations in the future.

22 Claims, 11 Drawing Sheets

(56) References Cited

U.S. PATENT DOCUMENTS

| | | | |
|---|---|---|---|
| 2008/0261776 A1 | 10/2008 | Skiba | |
| 2009/0154743 A1* | 6/2009 | Lundh | H04R 25/70 381/312 |
| 2011/0082519 A1* | 4/2011 | Strahl | A61N 1/37247 607/57 |
| 2011/0200217 A1* | 8/2011 | Gurin | A61B 5/123 381/320 |
| 2012/0029593 A1* | 2/2012 | Calle | A61N 1/36032 607/57 |
| 2012/0077158 A1 | 3/2012 | Jastrzembski et al. | |
| 2012/0155664 A1 | 6/2012 | Zhang et al. | |
| 2013/0137550 A1 | 5/2013 | Skinner et al. | |
| 2014/0050341 A1* | 2/2014 | Flynn | H04R 25/606 381/326 |
| 2014/0270210 A1 | 9/2014 | Van Dijk | |
| 2014/0309549 A1* | 10/2014 | Selig | H04R 1/1041 600/559 |
| 2016/0001077 A1* | 1/2016 | Pontoppidan | H04R 25/70 607/57 |
| 2017/0360364 A1* | 12/2017 | Heasman | A61B 5/04 |

* cited by examiner

HEARING PROSTHESIS EFFICACY ALTERING AND/OR FORECASTING TECHNIQUES

CROSS-REFERENCE TO RELATED APPLICATIONS

This application claims priority to Provisional U.S. Patent Application No. 62/081,165, entitled HEARING PROSTHESIS EFFICACY ALTERING AND/OR FORECASTING TECHNIQUES, filed on Nov. 18, 2014, naming Sean LINEAWEAVER of Gig Harbor, Wash., as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting. One type of medical device where there is utilitarian value in fitting such to an individual recipient is the above-noted cochlear implant. That said, other types of medical devices, such as other types of hearing prostheses, exist where there is utilitarian value in fitting such to the recipient.

SUMMARY

In accordance with an exemplary embodiment, there is a method of forecasting subjective efficacy of a hearing prosthesis implanted in a recipient, comprising subjecting a recipient to a plurality of temporally spaced aural tests, the aural tests evoking hearing percepts with the hearing prosthesis, obtaining first data indicative of the recipient's ability to hear with the hearing prosthesis based on performance by the recipient of the temporally spaced aural tests; and forecasting second data based on the first data, wherein the second data are indicative of the recipient's ability to hear with the hearing prosthesis at one or more temporal locations in the future.

In accordance with another exemplary embodiment, there is a method of altering a recipient's ability to hear with a hearing prosthesis implanted in a recipient, comprising subjecting a recipient who has participated in a plurality of respective temporally spaced aural training tasks to a plurality of respective temporally spaced aural tests, the respective aural tests evoking hearing percepts evoked by the hearing prosthesis, and influencing the recipient's commitment to performing subsequent aural training tasks based on first data relating to the aural tests.

In accordance with another exemplary embodiment, there is a non-transitory computer-readable media having recorded thereon, a computer program for executing at least a portion of a method of evaluating subjective efficacy of a hearing prosthesis implanted in a recipient, the computer program including code for obtaining first data indicative of the recipient's ability to hear with the hearing prosthesis based on empirical data of performance by the recipient of temporally spaced aural tests that evoked a hearing percept with the hearing prosthesis, code for obtaining a function based on the first data, and code for obtaining second data indicative of the subjective efficacy of the hearing prosthesis based on the function.

In accordance with another exemplary embodiment, there is a system for managing the subjective efficacy of a hearing prosthesis, comprising a processor and an input/output device configured to receive input indicative of the recipient's ability to hear with the hearing prosthesis, wherein the processor is configured to develop performance data based on the received input indicative of the recipient's ability to hear with the hearing prosthesis, and the processor is configured to develop hypothetical efficacy data indicative of a subjective hypothetical efficacy of the hearing prosthesis based on the developed performance data.

BRIEF DESCRIPTION OF THE DRAWINGS

Embodiments are described below with reference to the attached drawings, in which, with respect to the figures.

DETAILED DESCRIPTION

Figure 1:
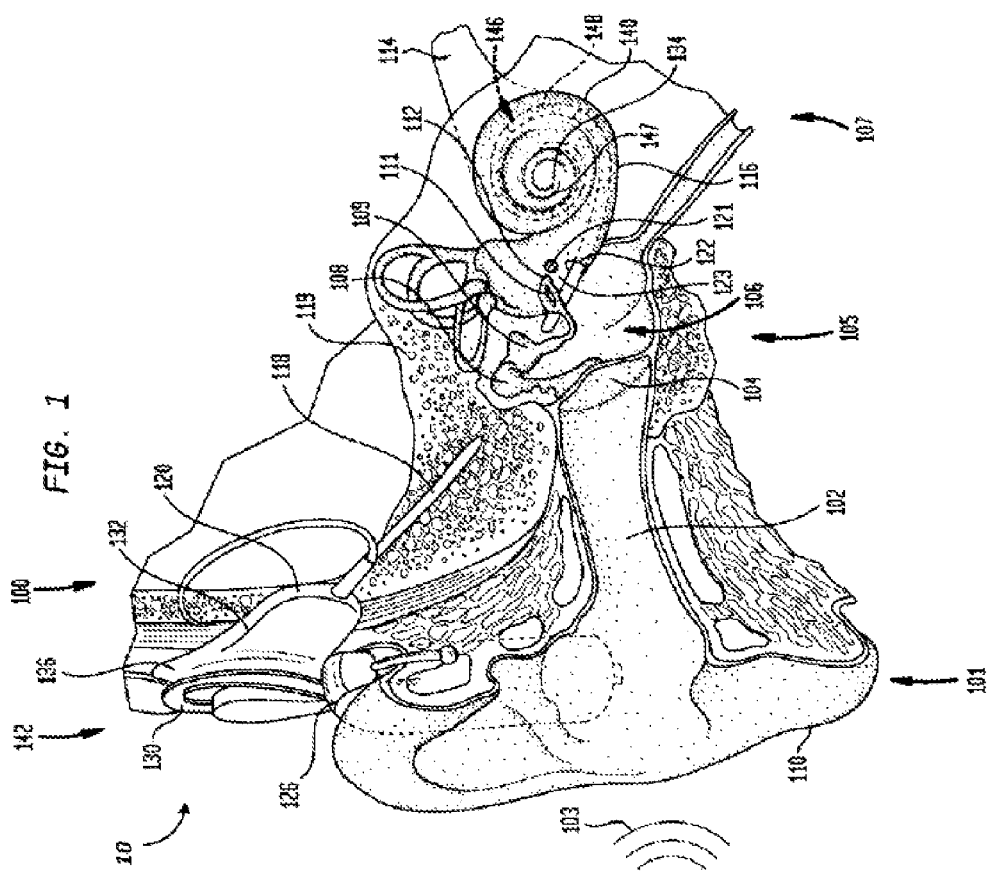
FIG. 1 is a perspective view of an exemplary hearing prosthesis in which at least some of the teachings detailed herein are applicable.

FIG. 1 is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.). Also, the teachings detailed herein are also applicable to other hearing prostheses, as will be detailed below.

The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery that is recharged by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand/or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand/or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

In an exemplary embodiment, subsequent implantation of the cochlear implant 100, the recipient can have the cochlear implant 100 fitted or customized to conform to the specific recipient desires/to have a configuration (e.g., by way of programming) that is more utilitarian than might otherwise be the case. Also, in an exemplary embodiment, methods can be executed with the cochlear implant 100, before and/or after it is fitted or customized to conform to the specific recipient desire, so as to alter (e.g., improve) the recipient's ability to hear with the cochlear implant 100 and/or so as to change an efficacy of the implanted cochlear implant 100 (e.g., improve). Some exemplary procedures along these lines are detailed below. These procedures are detailed in terms of a cochlear implant by way of example. It is noted that the below procedure is applicable, albeit perhaps in more general terms, to other types of hearing prosthesis, such as by way of example only and not by way of limitation, bone conduction devices (active transcutaneous bone conduction devices, passive transcutaneous bone conduction devices, percutaneous bone conduction devices), direct acoustic cochlear implants, sometimes referred to as middle-ear-implants, etc. Also, the below procedures can be applicable, again albeit perhaps in more general terms, to other types of devices that are used by a recipient, whether they be prosthetic or otherwise.

The cochlear implant 100 is, in an exemplary embodiment, an implant that enables a wide variety of fitting options and training options that can be customized for an individual recipient.

In an exemplary embodiment, the fitting methods detailed herein are executed in conjunction with a clinical professional, such as by way of example only and not by way of limitation, an audiologist, who selects a set of parameters, referred to herein as a parameter map or, more simply, a MAP, that will provide utilitarian sound reception for an individual recipient. That said, in an alternate embodiment, the fitting methods detailed herein are executed without a clinical professional, at least with respect to some of the method actions detailed herein. Additional details associated with the cooperation and lack of cooperation of a clinical professional are detailed below.

An exemplary embodiment entails fitting a device, such as a cochlear implant, to a recipient based at least in part on the ability of the recipient to perceive sound. Any method and/or system of fitting a cochlear implant can be utilized in at least some embodiments, and any device that can enable the method and/or system can be used in at least some embodiments.

An exemplary embodiment also entails altering the recipient's ability to hear with a hearing prosthesis, such as cochlear implant 100, implanted in the recipient by implementing strategies based on a function related to performance of the recipient vis-à-vis hearing with the prosthesis. Additional details of this will be presented below. First, however, an exemplary method will now be detailed.

Figure 2:
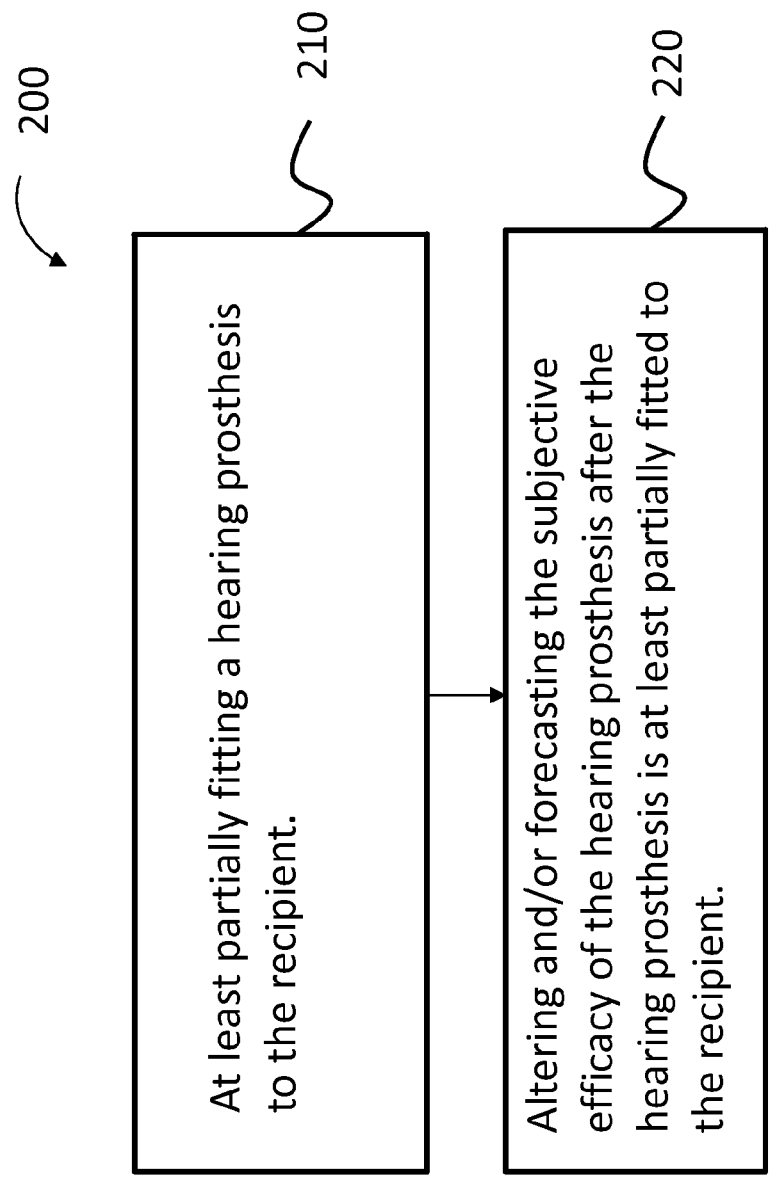
FIG. 2 presents an exemplary flowchart for an exemplary method according to an exemplary embodiment.

Referring now to FIG. 2, an exemplary flowchart is presented detailing an exemplary method 200 of altering the subjective efficacy of a hearing prosthesis implanted in a recipient, such as cochlear implant 100. Method 200 includes method action 210, which entails at least partially fitting the hearing prosthesis to the recipient. By way of example only and not by way of limitation, a genetic algorithm process can be used, such as algorithms detailed in the teachings of U.S. patent application publication number 2010/0152813 to Dr. Sean Lineaweaver, filed on Sep. 10, 2009. That said, in alternative embodiments, alternate methods and/or systems of fitting the hearing prosthesis to the recipient can be utilized. In an exemplary embodiment, method action 210 can be executed using any method and/or system that can enable the hearing prosthesis at issue to be fitted to the recipient.

In an exemplary embodiment, method action 210 can entail adjusting a structural and/or functional feature of the hearing prosthesis, thereby tailoring and/or customizing the hearing prosthesis for the specific needs, specific wants or specific characteristics of the recipient. In an exemplary embodiment, in the case of a cochlear implant or other hearing prosthesis, this can entail selecting a set of parameters that correspond to parameters where the recipient has had relative success, relative to other sets of parameters, in various tasks associated with the hearing prosthesis, adjusting or otherwise configuring the cochlear implant to operate utilizing that set of parameters.

Method action 210 further includes method action 220, which entails altering the subjective efficacy of the hearing prosthesis. As noted in FIG. 2, method action 220 is executed after the hearing prosthesis is at least partially fitted to the recipient (i.e., after method action 210 is executed).

An exemplary embodiment of method action 220 will be detailed below relating to altering the subjective efficacy of the hearing prosthesis. First, however, an exemplary method having applicability to method action 220 will now be detailed, which includes forecasting how the subjective efficacy will be altered (i.e., how well the recipient of the hearing prosthesis will be able to hear with the hearing prosthesis at some point in the future). In some embodiments, this method can be practiced to alter the subjective efficacy of the hearing prosthesis, while in other embodiments, this method is not utilized per se to alter the subjective efficacy of the hearing prosthesis, but instead utilized as a stand-alone method (subsequent to, in at least some embodiments, at least partially fitting the hearing prosthesis) relative to a method of altering the efficacy of the hearing prosthesis.

By subjective efficacy, it is meant to the efficacy of the hearing prosthesis with respect to an individual, specific, recipient, to which the prosthesis is attached and/or fitted. This is as opposed to a statistical efficacy, such as by way of example only and not by way of limitation, that which would be the case with respect to a very large population. By analogy, a drug can have a statistical efficacy such that a given result occurs and 99% or 99.9% of recipients of the drug. However, for a recipient in the 1% or 0.1%, the subjective efficacy does not correspond to that given result. In an exemplary embodiment, the subjective efficacy corresponds to the ability of the recipient to hear with the hearing prosthesis, all other environmental factors that are relevant being held equal. Better efficacy and/or improved efficacy corresponds to the recipient being able to hear better and or the recipient experiencing in improved hearing experience relative to another data point.

Figure 3:
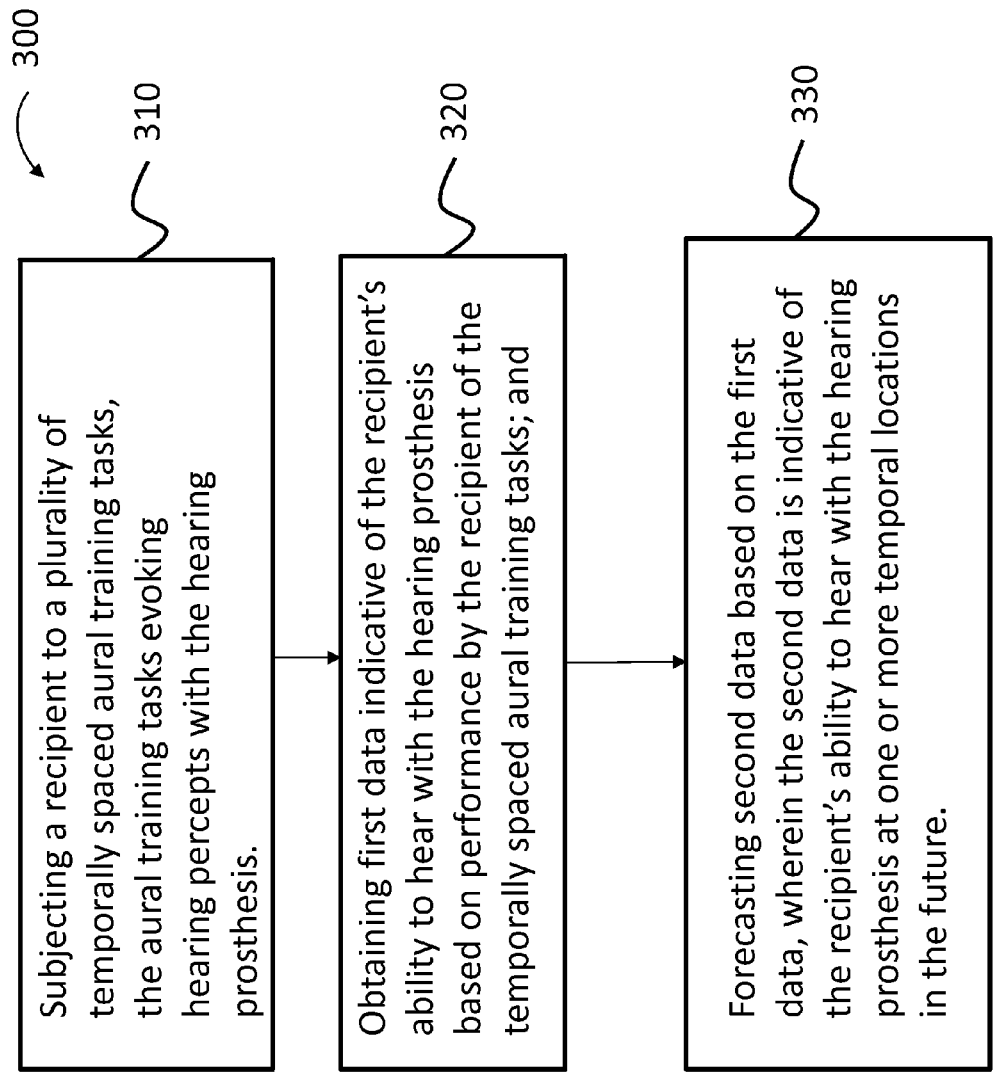
FIG. 3 presents another exemplary flowchart for an exemplary method according to an exemplary embodiment.

Referring now to FIG. 3, an exemplary flowchart is presented detailing an exemplary method 300 of forecasting subjective efficacy of a hearing prosthesis implanted in the recipient. Method 300 includes method action 310, which entails subjecting the recipient, who has undergone a plurality of respective temporally spaced aural training tasks, to a plurality of temporally spaced aural tests. In an exemplary embodiment, the aural training tasks are training tasks that are therapeutic with respect to habilitating and/or rehabilitating the ability of the recipient of the hearing prosthesis to hear with the hearing prosthesis. In an exemplary embodiment, the temporally spaced aural training tasks are tasks directed towards cognitive and/or neural rehabilitation and/or habilitation of the recipient. In an exemplary embodiment, the aural tests are measurements of the recipient's ability to hear with the hearing prosthesis.

It is noted that unless otherwise detailed herein, respective aural tests are temporally linked to respective aural training tasks. In at least some embodiments, an aural test is taken immediately before and immediately after a respective aural training task. (Additional details of this are described below.) In this vein, the temporal location(s) of aural tests can serve as a proxy for the temporal location of respective aural training tasks, and vice versa. For example, knowing the temporal location of a pre-aural training task, aural test and/or a post-aural training task aural task (depending on which one exits—both may exist) means that the temporal location of the respective aural training task is known, and visa-versa. Further, unless otherwise stated, the presence or existence of an aural test indicates the presence or existence of an aural training task and vice versa. In this regard, while embodiments of various methods are described in terms of subjecting the recipient to an aural test, at least some embodiments can include also subjecting the recipient to a respective aural training task. In an exemplary embodiment, this can include providing the tasks to the recipient, although in other embodiments, the aural training task is not provided to the recipient (it is obtained via another method).

By temporally spaced, it is meant for example that each task of the plurality of tasks is separated by a period of time that includes activities that are not associated with the aural training tasks. The same is the case with respect to the tests—each test of the plurality of tests is separated by a period of time that includes activities that are not associated with the aural tests (but aural training tasks are associated with aural tests, as the tests are used to generate data indicative of the efficacy of the hearing prosthesis, which is impacted with respect to training). In an exemplary embodiment, the aural training tasks respectively comprise training sessions with the hearing prostheses. In an exemplary embodiment, a given aural training task can last for a few minutes to a half hour or more (e.g. about 45 minutes, about an hour, etc.). Hours may pass in between one aural training task and another (e.g., a day, two days, a few days, a week, etc.). In between one aural training task and another aural training task, the recipient might sleep, might go to work, might exercise, etc., or otherwise engage in activities that do not constitute an aural training task.

By "subjecting the recipient to aural tests," it is meant that actions are taken that will result in the recipient taking the aural tests. In an exemplary embodiment, this can entail instructing the recipient to take the tests. In an exemplary embodiment, this can entail providing the recipient the tests. Indeed, in an exemplary embodiment, this can entail providing the recipient the underlying tools to take the test, partially or fully (e.g., providing the recipient with a system that enables the tests to be taken, prescribing a test to the recipient, etc.). Various embodiments described herein are described in terms of providing the recipient the tests. However, in view of the above, it will be understood that this is not the only way to subject the recipient to an aural test.

It is necessary to practice method action 310 such that the aural training tasks and aural tests evoke hearing percepts with the hearing prosthesis. That is, by way of example, when the recipient participates in the temporally spaced aural training tasks, the sounds generated by the aural training tasks are captured by the microphone of the cochlear implant 100. The same is the case with the aural tests. The cochlear implant 100 processes these captured sounds and generates electrical output signals to the cochlear electrode array to evoke a hearing percept based on the captured sound, and thus based on the sound provided in the aural training tasks and the aural tests. Indeed, in an exemplary embodiment, the only way that the recipient can hear the sounds presented during the aural training tasks and aural tests is due to the hearing prostheses. That is, in an exemplary embodiment, method action 310 is executed with a recipient that is completely (100%) deaf. That said, in an alternative embodiment, method action 310 is executed with a recipient that is only partially deaf. Moreover, in an alternative embodiment, method action 310 is executed with a recipient that has the ability to hear without the hearing prosthesis. Method action 310 can be executed with any type of recipient, provided that a hearing prosthesis is used to evoke a hearing percept.

In an exemplary embodiment, a given aural test entails presentation of the recipient with a series of words (singularly and/or in groups (such as in full sentences)), and having the recipient indicate his/her perception thereof, over a training period. This can be done through interaction of an audiologist (where, for example, the audiologist speaks the words in a manner sufficient for the hearing prosthesis to capture the words and evoke a hearing percept based on the captured words, or where the audiologist presents a recording or the like of the words, etc.) or through solo interaction with a device configured to enable the teachings detailed herein and/or variations thereof to be practiced, or at least configured such that method action 310 can be enabled. With respect to the latter, by way of example only and not by way of limitation, the device may be a personal computer that includes code to presents recordings and/or synthesized sounds of words. Further, with respect to the indication of the perception of the words presented to the recipient, the recipient can vocalize the perception and/or can write the perceived words and/or select the perceived words from a list of words, etc. Additional details of such devices, systems and/or methods of providing the recipient with a plurality of temporally spaced aural training task will be detailed below.

Method 300 further includes method action 320, which entails obtaining data indicative of the recipient's ability to hear with the hearing prosthesis based on performance by the recipient of the temporally spaced aural tests. In an exemplary embodiment, this is empirical data that is used, as will be detailed below, as a measure of progress to extrapolate and/or predict future performance if a given protocol is followed in the future.

As is clear from the just described method action, method action 320 cannot be practiced without the hearing prosthesis being utilized in method action 310. In an exemplary embodiment, the data indicative of the recipient's ability to hear with the hearing prosthesis includes quantitative and/or qualitative results of method action 310. In an exemplary embodiment, this entails scoring the recipient's performance on the tests presented in method action 310. By way of example only and not by way of limitation, the recipient can be scored based on the number of words and/or sentences correctly understood by the recipient. That said, in an alternative embodiment, method 320 is executed by simply obtaining results of method action 310. That is, in at least some embodiments, it is not required to obtain quantitative results. That is, other types of results can be obtained. By way of example only and not by way of limitation, in at least some embodiments, the results can entail obtaining the recipient feedback to the tests (e.g., information indicative of what the recipient perceives as being heard). It is further noted that in an alternate embodiment, method action 320 can be executed by simply obtaining the results of method action 310. That is, it is not necessary to actually score the recipient to execute method action 320. Instead, in this exemplary embodiment, it is only necessary to obtain the scores (i.e. the scoring can be performed outside of the method).

It is noted that in an exemplary embodiment, at least some of the methods detailed herein utilize quantitative testing/scoring as opposed to and/or in addition to qualitative testing (or judgment)/scoring.

It is noted that method actions 310 and 320 (and other method actions of method 300 and/or other method actions detailed herein) can be executed by a clinical professional, such as an audiologist or the like. That said, as will be detailed below, in an alternative embodiment, some or all of these methods can be executed in an automated or automatic manner. Still, according to at least some embodiments, method actions 310 and 320 will be executed in a clinical setting, wherein the tester (e.g., audiologist) presents words (including sentences) to the recipient that are used by the hearing prosthesis to evoke a hearing percept, and instructs or otherwise has the recipient attempt to repeat or otherwise identify (e.g., by writing or the like—again described in greater detail below) what he or she perceives as being heard. This is part of method action 310. The tester then scores the recipient as to how many words and/or sentences were accurately perceived. This is method action 320. Accordingly, the relationship between the tester and the recipient can be interactive, in that the tester presents the sound material to the recipient, and the recipient identifies the answers, followed by the tester scoring the recipient's feedback.

Accordingly, in an exemplary embodiment, the data indicative of the recipient's ability to hear with the hearing prosthesis can be a function related to training/performance. In an exemplary embodiment, the function is a function of time vs. performance. In an exemplary embodiment, time constitutes an average (mean) time between the aural training tasks, and performance constitutes an average (mean) score of the recipient on the aural training tasks. By way of example only and not by way of limitation, if the recipient's average time between method actions 310 was five days, and the recipient's average score was 33, the function would be 5/33 day/score, or 0.15 day/score. In an exemplary embodiment, performance constitutes an average (mean) improvement score of the recipient on aural tests. By way of example only and not by way of limitation, if the recipient's average score improved from 33 to 35, and the aforementioned temporal period is still applied, the function in would be 5/2 day/score, or 2.5 day/score. Alternatively, if the recipient's average score decreased from 33 to 31, the function would be −2.5 day/score.

Again, it is noted that the aforementioned functions are merely exemplary. In an exemplary embodiment, the data indicative of the recipient's ability to hear with the hearing prosthesis constitutes temporally specific data (e.g., training occurring on July 10 resulted in score 25, training occurring on July 17 resulted in score 30, training occurring on July 24 resulted in score 35, training occurring on July 29 resulted in score 32, etc.). Any type of data that can enable the teachings detailed herein and/or variations thereof can be obtained in method action 320 to enable the teachings detailed herein and/or variations thereof to be practiced.

It is further noted that the aforementioned functions can be based on more or fewer data points than those detailed above. In at least some exemplary embodiments, the more data points, the more accurate the aforementioned functions will be, at least providing that the data points are themselves accurate or otherwise not skewed in an abnormal way.

Still with reference to FIG. 2, method 300 includes method action 330, which entails forecasting additional data based on the data indicative of the recipient's ability to hear with the hearing prosthesis obtained in method action 320. In an exemplary embodiment, this additional data forecasted in method action 330 is indicative of the recipient's ability to hear with the hearing prosthesis at one or more temporal locations (e.g., on a given calendar day, a given number of days hence, etc.) in the future relative to the temporal location at which method action 330 is practiced. In an exemplary embodiment where the data obtained in method action 320 indicative of the recipient's ability to hear with the hearing prosthesis corresponds to a function, this function can be utilized to forecast the data in method action 330, and thus the forecasted data are based on the data obtained in method action 320. That said, method action 330 can also be based on other statistical indicators which qualify the forecast. For example, recognition that there is an ultimate limit to the ability of the recipient to hear with the hearing prosthesis at some point in the future can be utilized to forecast the data in method action 330. By way of example only and not by way of limitation, such recognition can entail recognizing that the best that the recipient can achieve is achieving a perfect score on a given aural training task). Still further by way of example only and not by way of limitation, such recognition can entail recognition that the function is a nonlinear function. Such can result in the utilization of a cubic spline or a polynomial regression analysis to forecast the data in method action 330. Any system and/or method of forecasting data indicative of the recipient's ability to hear the hearing prosthesis at one or more temporal locations in the future based on the data obtained in method action 320 can be utilized in at least some embodiments to practice method action 330.

Additional details about the function will be described below, but first, some alternate embodiments utilizing method 300 will now be described.

Figure 4:
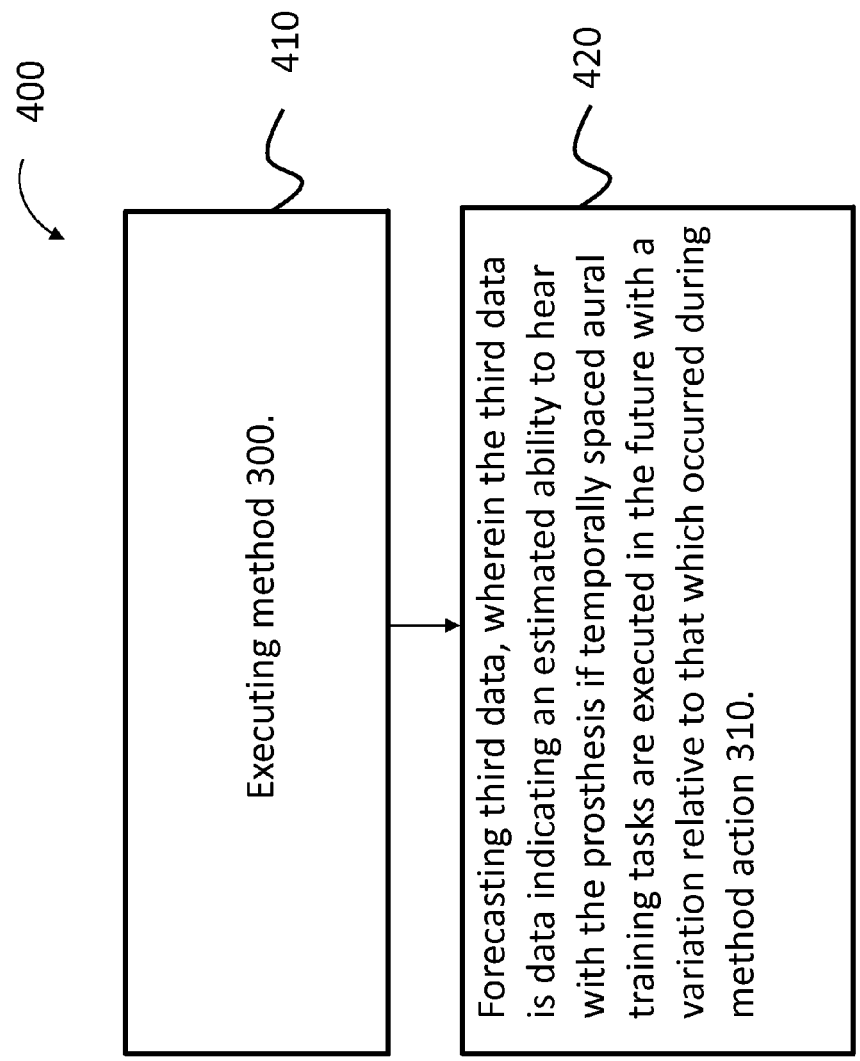
FIG. 4 presents another exemplary flowchart for an exemplary method according to an exemplary embodiment.

FIG. 4 presents a flowchart for another embodiment that utilizes method 300. Specifically, FIG. 4 presents a flowchart for a method 400, which includes method action 410 and method action 420. Method action 410 entails executing method 300. Method action 420 entails forecasting additional data (delta to the data forecasted in method action 410). The additional data forecasted in method action 420 is data indicating an estimated ability to hear with the prosthesis, if temporally spaced aural training tasks are executed in the future with a variation relative to that which occurred during method action 310. In an exemplary embodiment, method action 420 is executed utilizing the function developed in method action 320. By way of example only and not by way of limitation, the additional data forecasted in method action 420 entails data indicating an estimated ability to hear with the prosthesis if temporally spaced aural training tasks are executed in future with shortened temporal spacing between the tasks relative to that which previously occurred (i.e., the tasks upon which the data obtained in method action 320 is based). That is, in this exemplary embodiment, the timing between the various future tasks is shortened, where the timing corresponds to a hypothetical future training schedule. In an exemplary embodiment, the function mentioned above can be utilized to estimate the ability to hear with the prosthesis based on this hypothetical future training schedule. In at least some embodiments, the shortening of the temporal periods between the training tasks should, in theory, improve the recipient's ability to hear with the prosthesis relative to that which would be the case if the temporal period of the tasks of method action 310 is applied in the future schedule. That said, in at least some embodiments, it is possible that if the temporal period is shortened too much, the ability for the recipient to hear with the hearing prosthesis might actually be decreased relative to that which was the case if the temporal periods of the tasks of method action 310 were applied in the future schedule. Accordingly, an exemplary embodiment can also address this fact when executing method action 420.

Still further by way of example only and not by way of limitation, the additional data forecasted in method action 420 entails data indicating an estimated ability to hear with the prosthesis if temporally spaced aural training tasks are executed in future with lengthened temporal spacing between the tasks relative to that which previously occurred (i.e., the tasks upon which the data obtained in method action 320 is based). That is, in this exemplary embodiment, the timing between the various future tasks is lengthened. In an exemplary embodiment, the function mentioned above can be utilized to estimate the ability to hear with the prosthesis based on this hypothetical future training schedule. In at least some embodiments, the lengthened temporal periods between the training tasks should, in theory, reduce the recipient's ability to hear with the prosthesis relative to that which would be the case if the temporal period of the tasks of method action 310 are applied in the future schedule. That said, in at least some embodiments, it is possible that if the previous temporal period was too lengthy, the ability for the recipient to hear with the hearing prosthesis might actually be decreased relative to that which was the case if the temporal periods of the tasks of method action 310 were applied in the future schedule. Accordingly, an exemplary embodiment can also address this fact when executing method action 420.

It is noted that in the embodiments of FIG. 3 and FIG. 4, the timing between the tasks need not be constant. By way of example only and not by way of limitation, the number of days between tasks can be larger or smaller relative to the number of days between the tasks immediately precedent. A period of five days may elapse between tasks, followed by a period of three days that may elapse between tasks, followed by a period of two weeks that may elapse between tasks, followed by a period of one day that may elapse between tasks followed by a period of a few hours, etc. The aforementioned function noted above can take this into account. As will be detailed below, some exemplary embodiments take into account future hypothetical recipients availability and/or willingness to participate in training in executing method action 420.

Still with reference to FIG. 4, an alternate embodiment of a variation of the aural training tasks relative to that which occurred can entail using different training tasks. That is, instead of (or, in some embodiments, in addition to) varying the temporal period between the tasks, the type of tasks can be varied. In this vein, in an exemplary embodiment, the additional data forecasted in method action 420 entails data indicating an estimated ability to hear with the prosthesis if temporally spaced aural training tasks are executed in the future that are different relative to that which previously occurred. That is, in this exemplary embodiment, a different type of training may be applied (e.g., full sentences are utilized, partial sentences are utilized, different training techniques, different training programs, etc.). In an exemplary embodiment, the function mentioned above can be utilized to estimate the ability to hear with the prosthesis based on this hypothetical future training schedule using these different training techniques. That said, it is noted that in at least some embodiments, it is expected that the aural tests will be the same, so as to obtain an apples to apples comparison, although in other embodiments, the tests themselves may also change as well.

It is further noted that method action 420 can entail lengthening and/or shortening the period of the individual tasks relative to that which was the case when method action 310 was executed. It is further noted that the period of the individual tasks can be the same (uniform) in the forecasted schedule and/or can be different from one or more tasks relative to one or more other tasks in the future schedule. Indeed, it is noted that the different types of tasks noted above in the alternate embodiment can also be different from one or more future tasks to another one or more future tasks, thus forecasting the ability of the recipient to hear with hearing prosthesis if a change in the tasks are made at some point in the future (relative to those of method 310 and/or relative to those of a future task, which may or may not be different than those of method 310).

Figure 5:
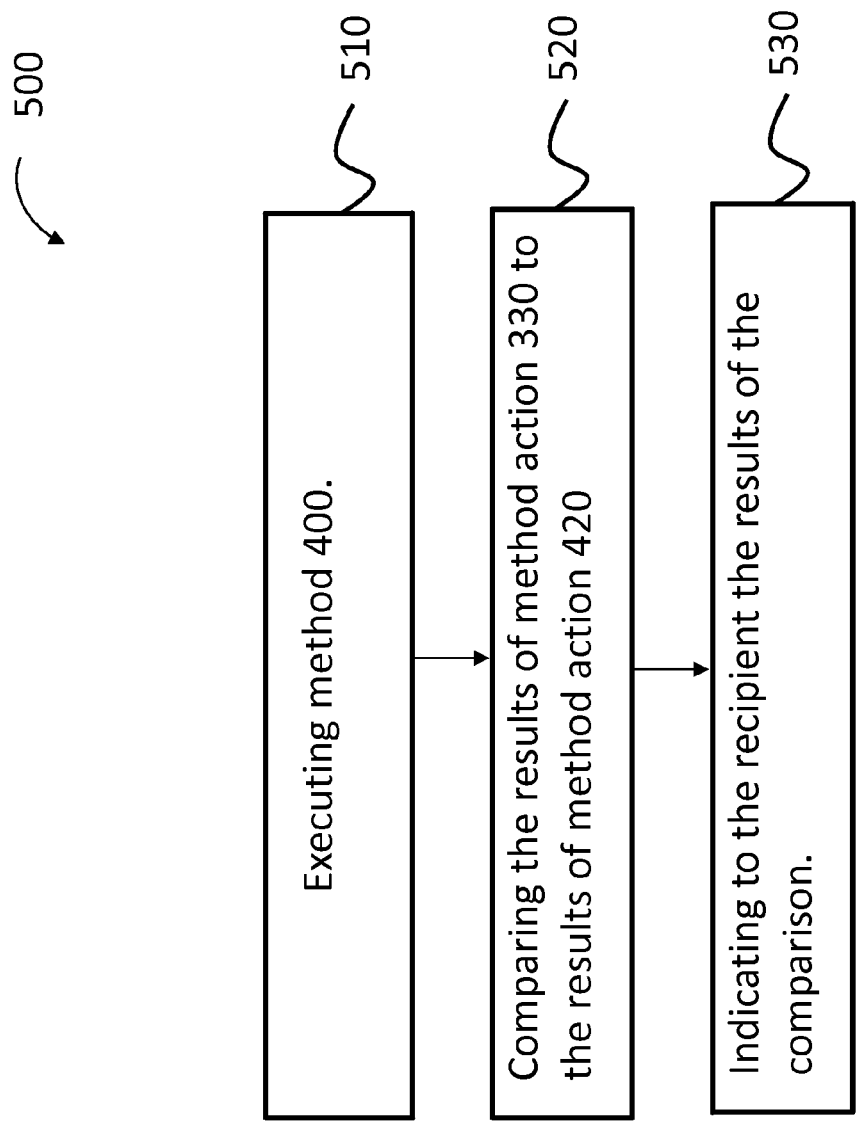
FIG. 5 presents another exemplary flowchart for an exemplary method according to an exemplary embodiment.

FIG. 5 depicts a flowchart for another alternate embodiment. Specifically, FIG. 5 presents a flowchart for method 500, which entails method action 510 and method action 520. Method action 510 entails executing method 400 as detailed above with respect to FIG. 4. Method action 520, which is executed after executing method action 510, entails comparing the results of method action 330 to the results of method action 420. In an exemplary embodiment, this entails comparing the forecast developed in method action 330 with the forecast developed in method action 420. Accordingly, an exemplary embodiment entails comparing (i) data indicating the estimated ability to hear with the prosthesis if the temporally spaced aural training tasks are executed in the future with the variation relative to that which occurred with respect to method action 310 (i.e., the data forecasted in method action 420) with (ii) data indicative of the recipient's ability to hear with hearing prosthesis at one or more temporal locations in the future based on the first data. In this exemplary embodiment, this can enable a forecast of the recipient's ability to hear with the hypothetical training schedule developed in method action 420 as compared to a forecast of the recipient's ability to hear with a hypothetical training schedule that corresponds to the training schedule associated with method action 310.

Method 500 further includes method action 530, which entails indicating to the recipient the effects of the variation of the tasks relative to that which would be the case if temporally spaced aural training tasks are executed in the future with the same temporal spacing between the tasks relative to that which was the case for the tasks upon which the first data are based. In an exemplary embodiment, this entails presenting a comparison of the hypothetical's future schedule with the shortened temporal periods to a hypothetical future schedule with the temporal periods used in method action 310. Alternatively and/or in addition to this, method action 530 can entail presenting a comparison of the hypothetical future schedule with different tasks to a hypothetical future schedule with the tasks used in method action 310.

As will be detailed further below, the presentation to the recipient can be performed utilizing a device and/or system configured to interact with the recipient and/or interact with an audiologist or the like, and, in at least some embodiments, one or more or all of the method actions of method 500

(including the sub-actions of the methods that feed into method 500) can be performed with such a device and/or system automatically. Again, additional details of this will be described below.

In view of the above, in at least some embodiments of method 300, method 300 further includes dynamically generating forecasts of data, wherein the dynamically generated forecasted data are indicative of the recipient's ability to hear with the hearing prosthesis at one or more temporal locations in the future. The dynamically generated forecasts can be used in method 500 as the results of method action 420.

An exemplary embodiment including the execution of any of methods 300, 400 and/or 500, can result in the recipient being more encouraged to continue and/or increase the training with the hearing prosthesis relative to that which would be the case in the absence of execution of any of these methods. Additional features of this phenomenon will be described below, but first, some additional subtasks of the methods 300 will be described.

More specifically, as noted above, method 300 includes method action 320, which entails obtaining data indicative of the recipient's ability to hear with the hearing prosthesis based on performance by the recipient of the temporally spaced aural tests of method action 310. Along the lines noted above, in an exemplary embodiment, method action 320 is executed by giving the recipient a test immediately before and/or immediately after a given aural training task. That is, in at least some embodiments, the data obtained in method action 320 is based on measurements of the ability the recipient to hear with the hearing prosthesis taken in close temporal proximity to at least one of the aural training tasks (e.g., immediately before and/or immediately after). In an exemplary embodiment, this is done with respect to every aural training task (before and/or after). That said, in some alternate embodiments, this is done with respect to only some of the aural training tasks. Any combination of measurements relative to the aural training tasks that can enable the teachings detailed herein and/or variations thereof to be practiced can be utilized in at least some embodiments.

In an exemplary embodiment, the data obtained in method action 320 is based on measurements of the ability of the recipient to hear with the hearing prosthesis taken in effective immediacy at least one of before or after at least one of the aural training tasks. In this regard, in an exemplary embodiment, the recipient, who has been fitted with the hearing prosthesis, takes an initial test that provides results (quantitative and/or qualitative) indicative of the recipient's ability to hear with the hearing prosthesis. The recipient then engages in the aural training task with little or no interruption between the initial test (pre-training test). The recipient then takes a subsequent test (post-training test) that provides results (quantitative and/or qualitative) indicative of the ability to hear with the hearing prosthesis, again with little or no interruption between the tasks and the subsequent test. By little or no interruption, it is meant that seconds, or at most, minutes, extend between the tasks and the test(s). That said, in an alternate embodiment, the period might be longer, but the recipient does not perform any substantive cognitive activity between the tests and the tasks (e.g., the recipient may go to the bathroom, the recipient might engage in small talk with the audiologist, the recipient might attend to a task (e.g., cleaning up a spill), etc., but no substantive cognitive activity occurs between the tests and the tasks). In this regard, in an exemplary embodiment, the data obtained in method action 320 is based on measurements of the ability of the recipient to hear with the hearing prosthesis taken at least one of before or after at least one of the aural training tasks without any cognitive stressors being located between the measurements and the at least one of the aural training tasks. Still further, in an exemplary embodiment, the data obtained in method action 320 is based on measurements of the ability of the recipient to hear with the hearing prosthesis taken at least one of before or after at least one of the aural training tasks without any intervening actions that could effectively skew the results of the measurements being located between the measurements and the at least one of the aural training tasks. In an exemplary embodiment, by effectively skew, it is meant that the measurements would be different in a substantive manner that affects the results of the methods detailed herein and/or variations thereof had those actions not taken place. In an exemplary embodiment, this is subjective to the recipient. In an alternative embodiment, this is based on statistical data relating to a class or group of recipients to which the recipient that is the subject of the method corresponds.

In an exemplary embodiment, the time period between the end of the pre-task test and the beginning of the task and/or the end of the task and the beginning of the post-task test is less than about 10, 20, 30, 40, 50, 60, 70, 80, 90, 110, 120 seconds, to a half minute, three minutes, 3½ minutes, four minutes, 4½ minutes, five minutes, about 10 minutes, about 20 minutes, about 30 minutes, about 45 minutes, about an hour, about an hour and a half, about 2 hours, about 2.5 hours, about 3 hours, about 4 hours and/or about 4.5 hours less or any value or range of values therebetween in about 5 second increments (25 seconds, 3 minutes and 15 seconds, between 35 seconds to 4 minutes and fifteen seconds, etc.). That said, in at least some exemplary embodiments, the time can extend to a day or more, albeit that is not in substantial temporal proximity to the tasks, especially, depending on the presence of cognitive stressors.

It is noted that method action 530 can have utilitarian value in that it can encourage the recipient to take the training/therapy more seriously and/or engage in more training/therapy and/or alter his or her training/therapy strategies, etc. For example, a comparison between the forecast of how well the recipient can hear with the hearing prosthesis based on different training/therapy schedules can encourage the recipient to follow one schedule versus another schedule (such as by way of example only and not by way of limitation, the schedule that forecast that the recipient will hear better with the hearing prosthesis sooner relative to the other schedule).

In this regard, at least some exemplary embodiments are directed towards increasing or otherwise sustaining a recipient's commitment to a given therapy and/or to encourage participation in future therapies. Along these lines, in at least some exemplary embodiments, via dedicated training, continued gains in performance with respect to listening with the hearing prosthesis can be obtained. This devotion to continued dedication can be proactively encouraged by utilizing empirically founded information such as that acquired as detailed above or by any other pertinent method that enables the teachings detailed herein to be practice. Moreover, in at least some embodiments, the teachings detailed herein and/or variations thereof can be utilized to demonstrate or otherwise forecast the results of curtailing a training program or the like. In this regard, method action 530 can result in instilling fear (or trepidation) or otherwise provide negative reinforcement to the recipient to change his or her therapy efforts.

Figure 6:
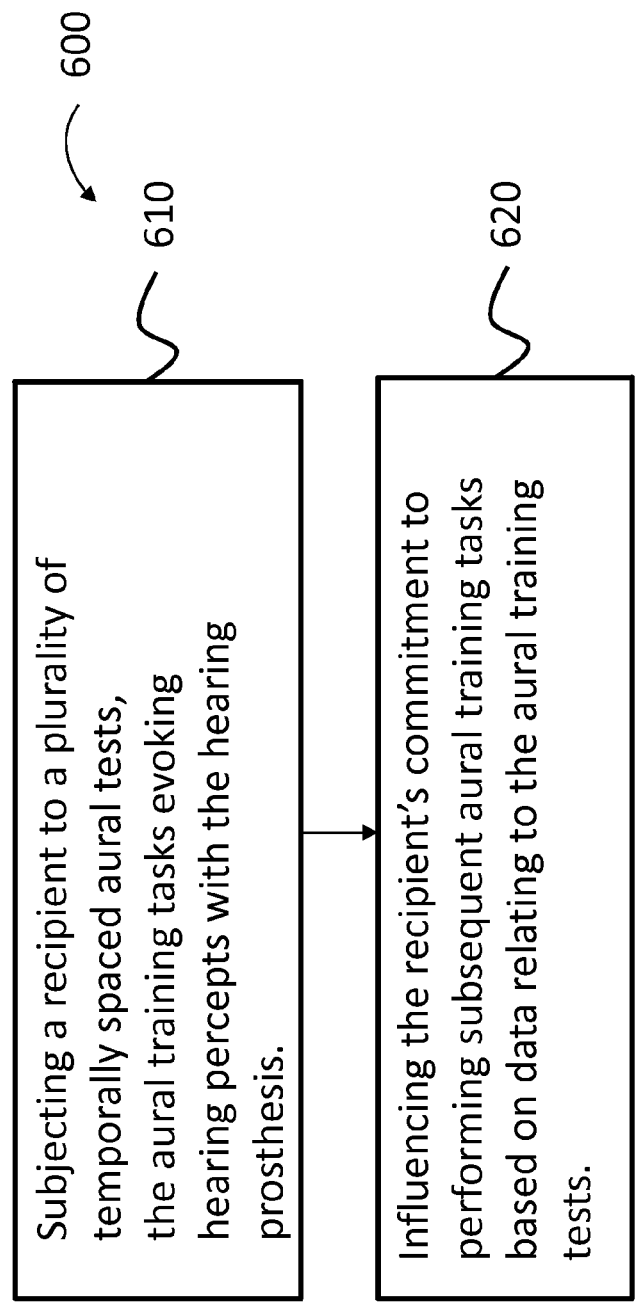
FIG. 6 presents another exemplary flowchart for an exemplary method according to an exemplary embodiment.

To this end, with reference back to FIG. 2, as noted above, method action 220 entails altering the subjective efficacy of the hearing prosthesis after the hearing prosthesis is at least partially fitted to the recipient. Method action 220 can be executed by executing method action 530, alone and/or in conjunction with one or more or all of the other method actions detailed herein and/or variations thereof. That said, in at least some embodiments, method action 220 can be executed separately with respect to method action 210. To this end, now with reference to FIG. 6, there is an exemplary method 600 (that can be practiced to execute method action 220 alone or in conjunction with method action 210) that includes method action 610, which entails subjecting a recipient with a plurality of temporally spaced aural tests. Again, it is noted that it is necessary for the aural tests to evoke hearing percepts by the hearing prosthesis. In this vein, method action 610 can be the same as method action 310 detailed above with respect to FIG. 3.

After executing method action 610, method 600 proceeds to method action 620, which entails influencing the recipient's commitment to performing subsequent aural training tasks based on data relating to the aural tests of method action 610 (or 310). In an exemplary embodiment, the data relating to the aural tests corresponds to the aforementioned function detailed above (again, additional details of which are described below). Accordingly, method 600 is a method of altering (e.g., improving) a recipient's ability to hear with a hearing prosthesis implanted in a recipient, at least relative to that which would be the case in the absence of the execution of method 600, or at least method action 620.

In an exemplary embodiment, method action 620 is executed by executing method action 530 as detailed above. That is, by way of example only and not by way of limitation, the forecast developed in method action 330 can be compared to the forecast developed in method action 420 (i.e., the extrapolated forecast based on continued training corresponding to that of method action 610 (or 310) can be compared to the forecast based on continued training that is different from that of method action 610 (or 310)). Thus, an exemplary embodiment reinforces the fact that aural therapy/training is an ongoing process, thereby ensuring or at least encouraging future progress by the recipient via future participation. For example, the recipient can be presented with a forecast that predicts how well the recipient will hear (corresponding to a first progress level) if the recipient follows a regime of shortened temporal spacing between training tasks and can be presented with a forecast that predicts how well the recipient will hear (corresponding to a second progress level, where one or both of the progress levels can correspond to negative progression (regression)) if the recipient follows a regime of temporal spacing between the training tasks corresponding to that of method action 310 and/or longer. In at least some embodiments, upon being presented with the two different forecasts (depicting the two different progress levels associated therewith)/two different sets of data, the recipient will be motivated to engage in a therapy/training regime that forecasts the better ability to hear with the hearing prosthesis (i.e., the progress level that results in more progress (including, in some instances, more negative progress/less regression)), and thus forecasts a better future subjective efficacy of the hearing prosthesis.

Indeed, in at least some embodiments, method action 620 entails presenting or otherwise demonstrating the negative impact/repercussions that interruption or cessation or a relaxation of a given training therapy can have on previously achieved performance gains. Accordingly, such can present negative repercussions to the recipient. That said, in an alternate embodiment, method action 620 can further entail presenting data indicative of positive repercussions to the recipient associated with the lack of an interruption or cessation or a relaxation of a given training therapy. The end result of all this is that the recipient's commitment to performing subsequent aural training tasks is influenced based on data relating to the aural training tasks.

It is noted that method action 620 can be practiced without a forecast of future hearing ability. In at least some embodiments, method action 620 can be executed by utilizing backward looking data. In this regard, in an exemplary embodiment, data indicating a difference in the ability to hear with the prosthesis relative to that which would be the case had different temporal spacing between respective aural training tasks occurred that are associated with method action 610. For example, the data can indicate that the recipient would not be able to hear as well with the hearing prosthesis had the temporal spacing between respective aural training tasks been greater than what was the case as related to method action 610. Alternatively, the data can indicate that the recipient would be able to hear better with the hearing prosthesis had the temporal spacing between respective aural training tasks been less than what was the case with respect to that which was related to method action 610.

Figure 7:
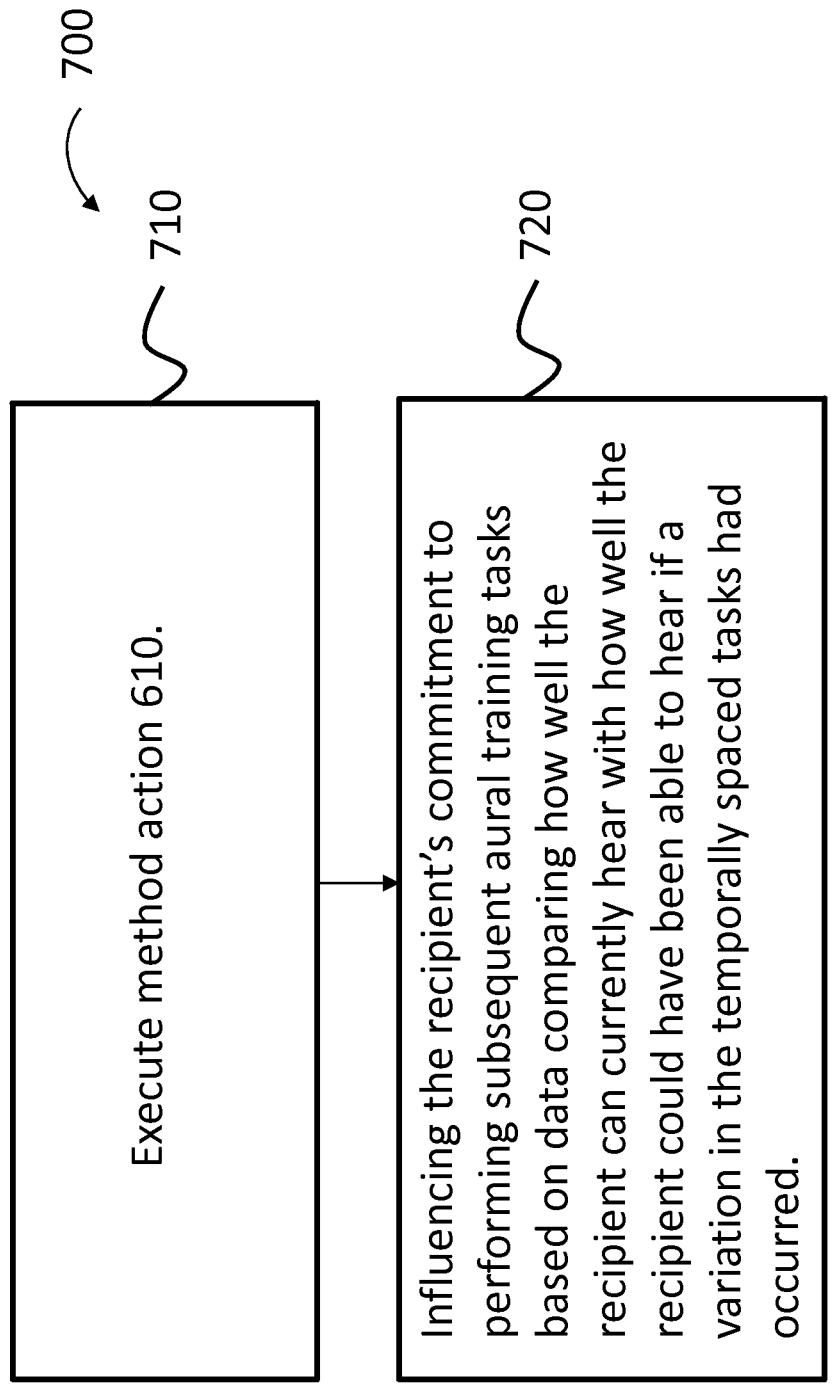
FIG. 7 presents another exemplary flowchart for an exemplary method according to an exemplary embodiment.

Consistent with method 400 detailed above, the data need not be based on differences in temporal spacing between the respective aural training tasks. Any variation relative to that which was related to method action 610 can be utilized. Accordingly, an exemplary embodiment entails indicating that the recipient would not be able to hear as well with the hearing prosthesis had the training tasks been executed in a manner different than that which was related to method action 610, and visa-versa. Again, consistent with method 400 detailed above, the length of the respective training task can be varied and/or the type of training tasks can be varied in order to present an indication of the recipient of how well the recipient would hear in the alternative scenarios relative to that which is the case based on the actual regime of method action 610. To this end, FIG. 7 presents an exemplary method 700 including method actions 710 and 720, where method action 710 entails executing method action 610 as detailed above, and method action 720 entails the aforementioned comparison.

In a similar vein, with respect to reducing the temporal period between the respective tasks, an exemplary embodiment entails executing method action 620 by indicating the difference in the ability to hear with the prosthesis relative to that which would be the case if additional and/or fewer aural training tasks had occurred relative to method action 610. Any variation in the temporally spaced training tasks that can enable the teachings detailed herein and/or variations thereof to be practiced can be utilized in at least some embodiments.

Figure 8:
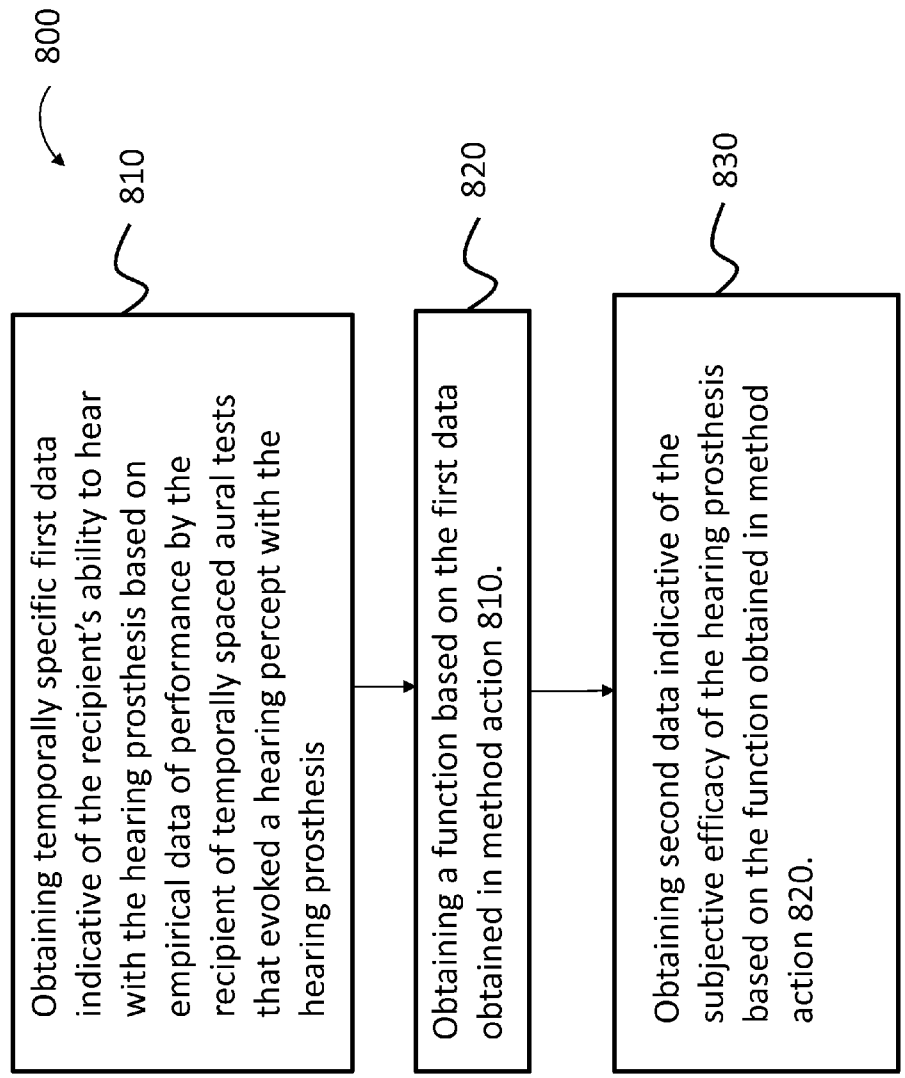
FIG. 8 presents another exemplary flowchart for an exemplary method according to an exemplary embodiment.

As noted above, at least some embodiments utilize the aforementioned function when implementing some of the method actions detailed above. FIG. 8 presents an exemplary flowchart for an exemplary method 800, usable in evaluating subjective efficiency of a hearing prosthesis implanted in a recipient. In particular, method 800 includes method action 810, which entails obtaining data (e.g., temporally specific data) indicative of the recipient's ability to hear with the hearing prosthesis based on empirical data of performance by the recipient of temporally spaced aural tests that evoked a hearing percept with the hearing prosthesis, where the tests can correspond to those of method action 310, for example. In an exemplary embodiment, method action 810 entails scoring the results of a prior test (the prior test corresponding to the empirical data of performance, where, in at least some embodiments, the test was taken in close temporal proximity to aural training tasks (before and/or after), as noted above) indicative of the ability of the recipient to hear with the hearing prosthesis, such as a test pertaining to the number of words and/or sentences correctly understood by the recipient. That said, in an alternative embodiment, method 810 is executed by simply obtaining the results of the tests. That is, it is not necessary to actually score the recipient to execute method action 810. Instead, in this exemplary embodiment, it is only necessary to obtain the scores (i.e. the scoring can be performed outside of the method). Thus, obtaining data indicative of the recipient's ability to hear Method 800 further includes method action 820, which entails obtaining a function based on the data obtained in method action 810. As noted above, the function can be a function of time vs. performance (length of time between training sessions, length of individual training sections, etc.) the function can be a function of type of training vs. performance, etc. Accordingly, in an exemplary embodiment, the empirical data of performance obtained in method action 810 is linked to temporal data or linked to training type data. The function can be a combination of these. Indeed, the function can be a multi-variable function. The function can also be based on other variables as well. Any variable that can enable the function to be utilized as detailed herein (e.g., to extrapolate a future prediction of future subjective efficacy of the hearing prosthesis, to estimate a prediction of current subjective efficacy of the hearing prosthesis relative to that which would be the case in other scenarios etc.) and/or variations thereof can be utilized to establish a function. As noted above, in an exemplary embodiment, the function is a training/performance function that demonstrates that every time training occurs, performance (subjective efficacy of the hearing prosthesis) improves to some degree, but regresses over time if no new training occurs, or at least if the period of time between training is longer than that which would be the case to avoid the regression, or at least an effective regression.

In an exemplary embodiment, method action 820 can entail automatically establishing a function utilizing various statistical and/or mathematical techniques based on the data obtained in method action 810. Computer programs of the like can be utilized to automatically establish the function (or functions—it is noted that in some embodiments, more than one function can be utilized, as will be detailed below). Any device, system and/or method that can enable a function to be developed or otherwise obtained to execute method action 820 can be utilized in at least some embodiments.

Method 800 further includes method action 820, which entails obtaining the data indicative of the subjective efficacy of the hearing prosthesis based on the function obtained in method action 820. In an exemplary embodiment, the obtained data are indicative of a hypothetical subjective efficacy. For example, the data can be the aforementioned forecast of the efficacy of the hearing prosthesis at some point in the future. Alternatively and/or in addition to this, the data can be a hypothetical subjective efficacy at the current time if an alternative training schedule and/or regime had been implemented. Accordingly, in at least some embodiments, obtained data indicative of the subjective efficacy of the hearing prosthesis based on the function obtained in method action 820 is also based on other data, such as by way of example only and not by way of limitation, temporal schedule of a future training regime. Some additional details of method 800 will now be detailed.

Figure 9:
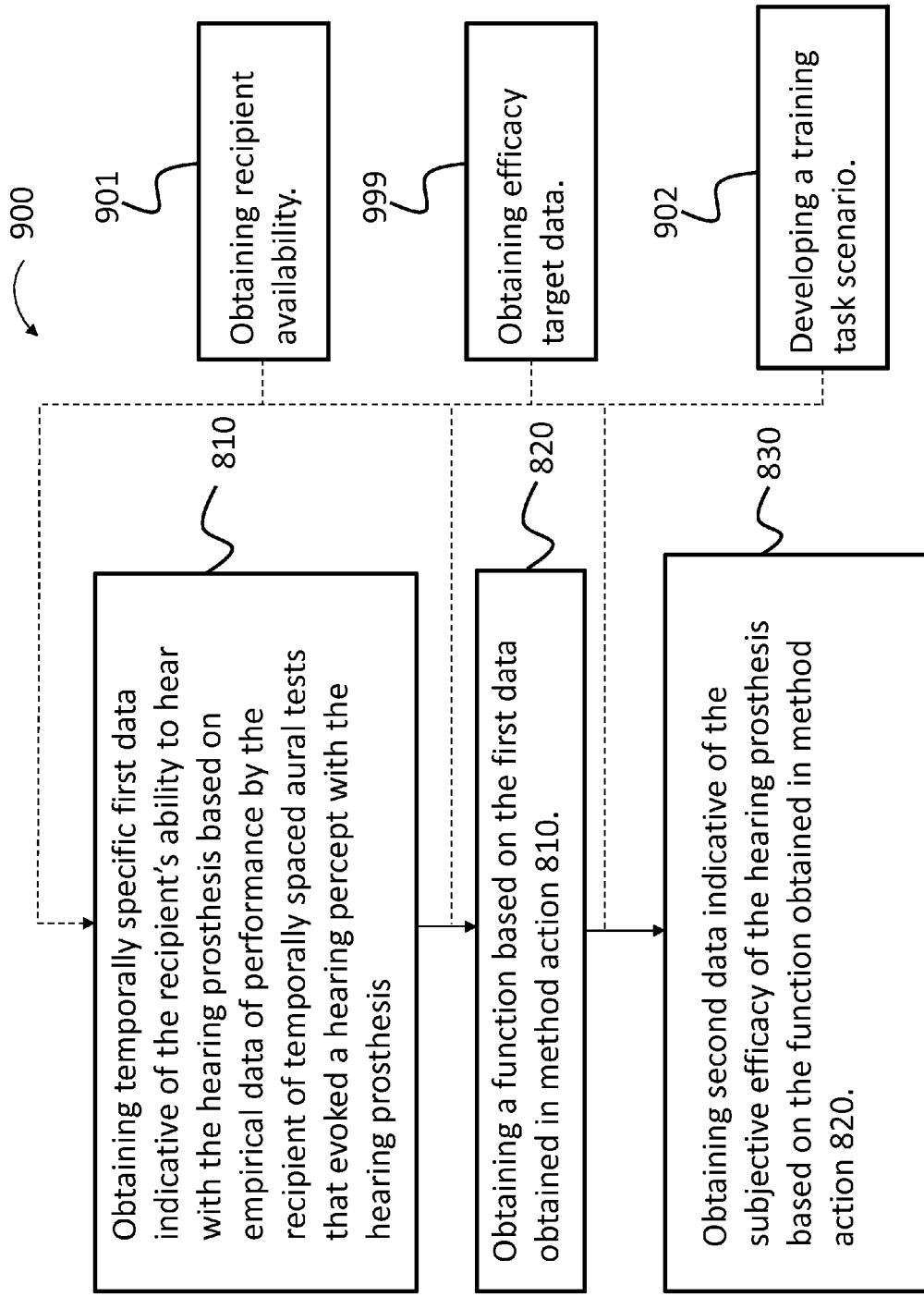
FIG. 9 presents another exemplary flowchart for an exemplary method according to an exemplary embodiment.

In an exemplary embodiment, method action 830 is executed based on data indicative of recipient availability which is indicative of future temporal periods in which the recipient will be able to participate in training with the hearing prosthesis. Accordingly, FIG. 9 presents an exemplary method 900, which includes the method actions of method 800 detailed above, and further includes, in an exemplary embodiment, method action 901, which entails obtaining recipient availability data that is indicative of the aforementioned future temporal periods of availability/participation. This action can be performed any time during method 800 at least before method action 830 is executed. Further, in an exemplary embodiment, method 900 includes method action 902, which entails developing a future training task scenario based on the recipient availability data and based on the aforementioned function developed in method action 820. This action can also be performed any time during method 800, at least before method action 830, at least providing that it is performed after method action 901. Accordingly, in an exemplary embodiment, method action 830 entails obtaining data indicative of the subjective efficacy of the hearing prosthesis at a future temporal period based on the future training task scenario developed. In this regard, in an exemplary embodiment, the function developed in method action 820 is utilized in conjunction with the recipient's availability to forecast the future subjective efficacy of the hearing prosthesis that is forecasted to result if the training schedule is followed. Along these lines, in an exemplary embodiment, this can provide encouragement to the recipient to continue a given training schedule and/or change to a new training schedule or otherwise provide the establishment of goals for the recipient that are realistic, which will also encourage the recipient to continue training by not discouraging the recipient from continuing training.

It is noted that the aforementioned action of obtaining recipient availability data can be executed by obtaining hypothetical recipient availability data. That is, by way of example only and not by way of limitation, the recipient availability data can correspond to a "dummy" schedule. Of course, in an alternate embodiment, the recipient availability data can correspond to an actual schedule, where the recipient will actually be available with respect to the future temporal periods.

FIG. 9 also presents method action 999, which entails obtaining hearing prosthesis subjective efficacy target data, which, in an exemplary embodiment can be future subjective efficacy target data. As with method actions 901 and method action 902, method action 999 can be practiced anytime during method 800, at least before method action 830. In an exemplary embodiment, the method action 999 can correspond to inputting a hypothetical goal for the subjective efficacy of the hearing prosthesis and/or a goal for the subjective efficacy the hearing prosthesis. As noted above, the goal can be temporally based. That is, the obtained target data can have a quantitative and/or qualitative value associated with the desired efficacy linked to a date at some point in the future or in the past or at present, depending on the desired data obtained in method action 830. For example, the target data can be linked to a date one or two or more weeks and/or to a date one or two or more months, etc., in the future. Accordingly, when method action 902 is executed, which entails developing a future training task scenario that, in this particular embodiment, is based on the target data obtained in method action 999, a training task scenario based on the target data can be developed. Alternatively and/or in addition to this, an exemplary embodiment, the obtained efficacy target data in method action 999 is linked to a current date, where the training task scenario developed in method action 902 presents a training scenario that would have had to have been implemented to achieve the efficacy target of the hearing prostheses. In this regard, method action 830 entails utilizing the function obtained in method action 820 to obtain the data indicative of the subjective efficacy of the hearing prostheses that corresponds to the efficacy target data of method action 999. In an exemplary embodiment, method action 830 can be performed by iterating various training task scenarios to arrive at a subjective efficacy corresponding to that obtained in method action 999, or can be performed by working backwards (the data indicative of the subject of efficacy the hearing prosthesis is obtained based on the function obtained in method action 820 because that function is used to develop the training task scenario that results in the second data indicative of the subjective efficacy of the hearing prosthesis).

It is noted that in an alternate embodiment of method 900, all of method actions 901, 902, and 999 can be executed. In this regard, in an exemplary embodiment, method 900 can be utilized to determine whether or not the recipient availability will result in the achievements of the subjective efficacy target data. Accordingly, in an exemplary embodiment, method 900 can be utilized to ascertain whether or not a future training schedule should be modified to achieve a target efficacy and/or to develop a future training schedule that will achieve a desired efficacy target. In an exemplary embodiment, the recipient availability can be obtained via iterative process and/or via an automatic process of generating hypothetical recipient availability dates (e.g., generating a schedule where the recipient should make himself or herself available on given dates to achieve the target efficacy). Further, in at least some exemplary embodiments, method 900 can be practiced with two or more future training task scenarios and/or past training task scenarios so as to obtain data indicative of a plurality of respective hypothetical efficacies of the hearing prosthesis that are linked to respective alternate hypothetical future training task scenarios and/or past training task scenarios. In an exemplary embodiment, comparisons between the respective efficacies of the respective training task scenarios can be presented to the recipient to show the recipient what could have been the case and/or what could be the case for a given training scenario.

In view of the above, it can be seen that in at least some embodiments, method 900 can be utilized to encourage or otherwise reinforce the recipient's commitment to a given training regime. Method 900 can be utilized to show the recipient what could have been the case if the recipient had undertaken a different training regime in the past (which could be positive reinforcement and/or negative reinforcement, depending on whether or not the different training regime would have produced a less efficacious result or a more efficacious result, relative to that which was the actual result). Method 900 can also be utilized to show the recipient what will happen in the future if the recipient continues with his or her prior training regime (again, which can be positive reinforcement and/or negative reinforcement, depending on whether or not the current training regime will produce a less efficacious results or a more efficacious result, relative to a hypothetical alternative training regime). In this regard, method 900 can be utilized to encourage the recipient to keep on training (not give up or slacken off) and/or to step up training. That said, in an alternate embodiment, method 900 can be utilized to plan around life events of the recipient. In some exemplary scenarios, there will be some temporal periods where recipient cannot perform training or otherwise will find it extremely difficult or otherwise distracting from other goals to perform training (e.g., recovery from surgery, involvement in an election having a date certain, involvement in the filming of a movie with a condensed and intense filing schedule, the recipient is going camping without electricity for an extended period of time, etc.). Accordingly, method 900 can be utilized to develop an alternate schedule/ workaround schedule to minimize any regression that may result due to these "blackout" periods.

It is further noted that in an exemplary embodiment, method 900 includes recommending an alternative training task scenario from a plurality of alternate training task scenarios based on a comparison of the efficacy that is linked to the test scenarios. It is noted that the action of comparing the efficacy of the training task scenarios may not necessarily require that the most efficacious training scenario be implemented. Accordingly, in an exemplary embodiment, the action of recommending an alternative training task scenario entails evaluating the subjective abilities and/or life events and/or desires of the recipient to recommend an alternative training task scenario. By way of example only and not by way of limitation, in some instances, a recipient very well may be able to achieve a higher level of efficacy with respect to his or her schedule, but the recipient finds that the schedule is tiring such that it interferes with another cognitive effort to the recipient (e.g., studying, work performance, forecasting stock prices, etc.) or otherwise interferes with other goals of the recipient (e.g., working overtime, exercising, participating in a sport, studying, etc.). Accordingly, the recommended alternate training task schedule can be a training schedule that takes into account these extraneous life facts of the recipient. That is, the alternative training task scenario can be a training task scenario that is the next best alternative to one or more alternate test scenarios that would result in a higher efficacy of the hearing prosthesis at a given point in the future, all other aspects being equal.

It is further noted that in at least some embodiments, through the analysis of the empirical testing data, utilizing the aforementioned function(s), some or all of the methods detailed herein can be used to analyze the degree and/or the functional nature (logarithmic, exponential, etc.) of rise or decrease in efficacy with respect to a given training scenario relative to another trainings scenario. In an exemplary embodiment, the degree and/or functional nature can be utilized to encourage and/or discourage the recipient from taking additional actions. Indeed, by way of example only and not by way of limitation, an exponential decrease in the efficacy of the hearing prosthesis resulting from a slackening and/or complete stop to training should be relatively more frightening to the recipient than a linear decrease in the efficacy of the hearing prosthesis.

It is further noted that in at least some embodiments, the forecasted efficacy can be presented in terms relative to a natural baseline which exists or otherwise should exist. In this regard, in at least some embodiments, the subjective efficacy of a hearing prosthesis will increase over time as a result of natural listening experiences, with or without training. Accordingly, in an exemplary, the data presented to the recipient that is directed to encouraging or discouraging training scenarios can be presented relative to the baseline. For example, a forecast that shows improvement might be discounted by presenting data to the recipient indicating that at least a portion of the forecast is unrelated to the training. Alternatively and/or in addition to this, a forecast can be further modified by removing baseline data (e.g., making the forecast look worse than it actually would be in an attempt to encourage the recipient to embark on a given training regime and/or avoid a given training regime).

It is noted that in at least some embodiments, the larger the sets of aural tests, and thus the larger the sets of data relating to the aural tests, the more reliable the forecast will be, and probability margins will tighten. Corollary to this is that in at least some embodiments, probability margins can also be presented to the recipient. In fact, worst-case and/or best case probabilities can be utilized depending on which training scenario the recipient is to be encouraged to follow.

In at least some embodiments, some or all of the method actions detailed herein and/or variations thereof are directed towards demonstrating the dynamic relationship between training and the subjective efficacy of the hearing prosthesis. Utilizing some or all of the method actions detailed herein and/or variations thereof, the positive impact of previously completed training on the efficacy of the hearing prosthesis and/or, alternatively, the negative consequences of not following the training schedule on the efficacy of the hearing prosthesis, can be demonstrated.

As noted above, embodiments can include presenting comparisons of hearing prosthesis efficacy and/or forecasts of hearing prosthesis efficacy to the recipient. These can be presented any media form that can convey the comparisons and/or forecasts, etc. to the recipient. In an exemplary embodiment, the comparisons and/or forecasts are presented utilizing graphs. In other embodiments, the comparisons and/or forecasts are presented using charts, and/or data tables, etc. In at least some embodiments, the comparisons and/or forecasts are presented using text. In some embodiments, these are presented in an automated manner, while in other embodiments, there presented in a more traditional manner. Any device, system and/or method of presenting the comparisons and/or forecasts the recipient can be utilized in at least some embodiments, providing that the teachings detailed herein and/or variations thereof can be enabled.

It is further noted that in at least some embodiments, the material presented to the recipient emphasize that the data presented thereto is based on each recipient's own heuristic evidence and behavior.

It is noted that some or all of the methods related to the aural tests are independent of specific training software and/or methods utilized to implement the training tasks. By way of example only and not by way of limitation, in embodiments of the methods detailed herein implemented via software, the software can be separate from software utilized to implements the aural training tasks. That said, in an alternate embodiment, methods include combined software. With regard to the latter, at least some embodiments can utilize standard clinician mediated testing software and a standard quantitative scoring paradigm, where the standard quantitative scoring paradigm is utilized to obtain data indicative of the results of the aural tests provided to the recipient. Indeed, in at least some embodiments, the testing can be automated, at least partially, in the recipient can interact with the software directly. That said, in an alternate embodiment, a clinician, such as an audiologist, can participate in the methods.

An exemplary system and an exemplary device/devices that can enable the teachings detailed herein, which in at least some embodiments can utilize automation, will now be described in the context of a recipient operated system. That is, an exemplary embodiment includes executing one or more or all of the methods detailed herein and variations thereof, at least in part, by a recipient.

Figure 10:
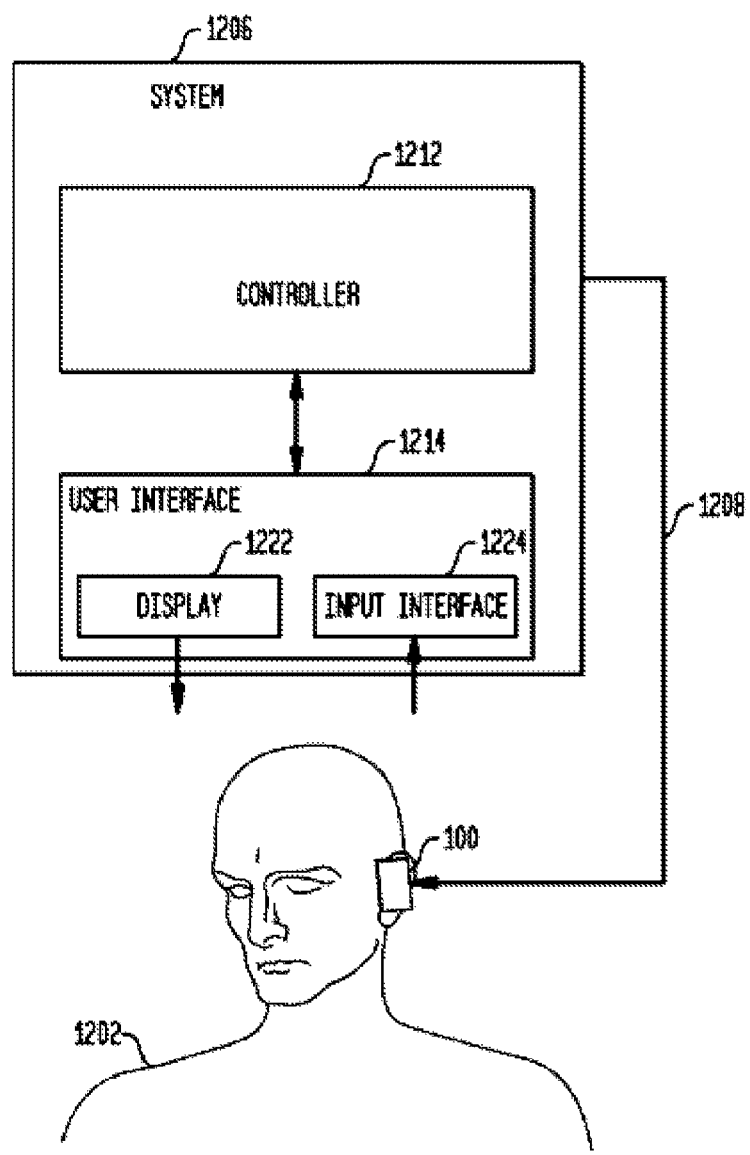
FIG. 10 presents an exemplary functional schematic of a system according to an exemplary embodiment, with which one or more or all of the various method actions detailed herein can be implemented.

FIG. 10 is a schematic diagram illustrating one exemplary arrangement in which system 1206 can be used to execute one or more or all of the method actions detailed herein in conjunction with the use of a hearing prosthesis, such as cochlear implant system 100. System 1206 will be described, at least in part, in terms of interaction with a recipient. In an exemplary embodiment, system 1206 is a recipient controlled system. Indeed, in at least some exemplary embodiments, the implementation of some or all the methods detailed herein and/or variations thereof is recipient directed, at least in part. That said, in at least some exemplary alternative embodiments, the implementation of some or all of the methods detailed herein and/or variations thereof is clinician directed, at least in part.

In an exemplary embodiment, system 1206 can be a fitting system having additional functionality according to the method actions detailed herein, or at least can be a system that has the functionality of a fitting system. In the embodiment illustrated in FIG. 10, the cochlear implant system can be directly connected to system 1206 to establish a data communication link 1208 between the speech processor 116 and system 1206. System 1206 is thereafter bi-directionally coupled by a data communication link 1208 with speech processor 116. While the embodiment depicted in FIG. 10 depicts a system 1206 and a hearing prosthesis connected via a cable, any communications link that will enable the teachings detailed herein that will communicably couple the implant and system can be utilized in at least some embodiments.

System 1206 can comprise a system controller 1212 as well as a user interface 1214. Controller 1212 can be any type of device capable of executing instructions such as, for example, a general or special purpose computer, a handheld computer (e.g., personal digital assistant (PDA)), digital electronic circuitry, integrated circuitry, specially designed ASICs (application specific integrated circuits), firmware, software, and/or combinations thereof. As will be detailed below, in an exemplary embodiment, controller 1212 is a processor. Controller 1212 can further comprise an interface for establishing the data communications link 1208 with the device 100 (e.g., cochlear implant 100). In embodiments in which controller 1212 comprises a computer, this interface may be for example, internal or external to the computer. For example, in an embodiment, controller 1206 and cochlear implant may each comprise a USB, Firewire, Bluetooth, WiFi, or other communications interface through which data communications link 1208 may be established. Controller 1212 can further comprise a storage device for use in storing information. This storage device can be for example, volatile or non-volatile storage, such as, for example, random access memory, solid state storage, magnetic storage, holographic storage, etc.

User interface 1214 can comprise a display 1222 and an input interface 1224. Display 1222 can be, for example, any type of display device, such as, for example, those commonly used with computer systems. In an exemplary embodiment, element 1222 corresponds to a device configured to visually display a plurality of words to the recipient 1202 (which includes sentences), as detailed above.

In an exemplary embodiment, user interface 1214 is configured to receive one or more or all of the data as detailed herein and/or variations thereof. By way of example only and not by way of limitation, the interface can enable a clinician and/or a recipient to input an existing training schedule and/or temporal periods of availability, etc. In an exemplary embodiment, as will be described in greater detail below, user interface 1214 is configured to enable the recipient to input data relating to the aural tests. In an exemplary embodiment, user interface 1214 is configured to receive the recipient answers to the aural tests. It is further noted that in an exemplary embodiment, user interface 1214 is configured to provide the test to the recipient.

Input interface 1224 can be any type of interface capable of receiving information from a patient, such as, for example, a computer keyboard, mouse, voice-responsive software, touchscreen (e.g., integrated with display 1222), microphone (e.g. optionally coupled with voice recognition software or the like) retinal control, joystick, and any other data entry or data presentation formats now or later developed. It is noted that in an exemplary embodiment, display 1222 and input interface 1224 can be the same component, e.g., in the case of a touch screen). In an exemplary embodiment, input interface 1224 is a device configured to receive input from the recipient indicative of a choice of one or more of the plurality of words presented by display 1222.

In an exemplary embodiment, display 1222 is configured to display some or all of the information conveyed to the recipient detailed herein. By way of example only and not by way of limitation, in an exemplary embodiment, display 1222 is configured to display a graph showing forecasted efficacy of the hearing prosthesis relative to time for a given training scenario. That said, alternatively and/or in addition to this, the user interface 1214 is configured to provide aural data.

Of course, in some embodiments, the system is configured to present to the recipient an audible word or a plurality of words or a sentence of words so that the testing actions detailed herein can be performed.

It is noted that in at least some exemplary embodiments, the system 1206 is configured to execute one or more or all of the method actions detailed herein, where the various sub-components of the system 1206 are utilized in their traditional manner relative to the given method actions detailed herein. By way of example only and not by way of limitation, the controller 1212 of the system 1206 is configured to obtain the data indicative of the forecasted efficacy. In this regard, by "obtain," it is meant by way of example that the controller 1212, which can correspond to a processor in at least some embodiments, calculates the data itself (thus obtaining the data).

In an exemplary embodiment, system 1206 is further configured to present to the device 100 (e.g., cochlear implant 100) and audible word or a plurality of words or a sentence of words. An exemplary embodiment, the audible sentence corresponds to the sentence previously presented to the recipient. By "audible sentence," it is meant a sentence that evokes a hearing percept by the hearing prosthesis 100. An exemplary embodiment, system 1206 includes a speaker or the like which generates an acoustic signal corresponding to the audible sentence that is picked up by a microphone of the hearing prosthesis 100. In an alternate embodiment, system 1206 is configured to provide a non-acoustic signal (e.g., an electrical signal) to the hearing prosthesis processor by bypassing the microphone thereof, thereby presenting an audible sentence to the hearing prosthesis. It is noted that in an exemplary embodiment, the information pertaining to word perception is based on the presented audible sentence. Along these lines, in an exemplary embodiment, the system 1206 is configured to receive input from the recipient indicative of perceived word(s) and/or sentences in response to presentation of the audible word(s) or sentences, thus enabling the teachings detailed above with respect to providing a recipient the ability to select from a plurality of sentences presented on a video screen of the like, such as may be the case by way of example only and not by way of limitation, in embodiments of the system that are configured to receive data indicative of the results of the aural tests (discussed in greater detail below). In an exemplary embodiment, this can be achieved via the input interface 1224. More specifically, a touchscreen or the like can be utilized as input interface 1224. Accordingly, in an exemplary embodiment, the system 1206 is configured to visually display a plurality of word(s) and/or sentences to the recipient, where at least one of the plurality of sentences displayed to the recipient corresponds to the audible word(s) and/or sentences. In this exemplary embodiment, the system 1206 is configured to receive input from the recipient indicative of a choice of one of the plurality of word(s) or sentences. That said, in an alternate embodiment, a microphone of the like can be utilized to receive vocalized input from the recipient. When coupled with speech recognition software or otherwise automated speech recognition algorithm or the like, the recipient's audible responses can be utilized as input from the recipient indicative of a perceived word(s) or sentences. Any device, system and/or method that is configured to receive input from the recipient can be utilized in at least some embodiments.

It is further noted that in at least some embodiments, the speech recognition algorithm can be coupled with a feedback system that presents information to the recipient indicative of what the speech recognition algorithm perceived as being spoken by the recipient. In this manner, the recipient can be provided with an indication of what the system perceived as being spoken, and can correct the system with respect to what the recipient actually said if there is a misperception (e.g., by the recipient repeating the words, the recipient typing in the actual words, etc.).

An exemplary embodiment, processor 1212 is configured to evaluate the received input for congruence between the perceived word(s)/sentence and the audible word(s)/sentence. In an exemplary embodiment, this entails comparing the word(s)/sentence that the recipient touched on the touchscreen to the word(s)/sentence forming the basis of the audible sentence. In an alternate exemplary embodiment this entails comparing data from speech recognition software based on the recipient's response captured by microphone with the word(s)/sentence forming the basis of the audible sentence.

More specifically, with reference to the system 1206, in an exemplary embodiment, system 1206 is a system for managing the subjective efficacy of a hearing prosthesis. In an exemplary embodiment, the user interface 1214 is an input/output device configured to receive input indicative of the recipient's ability to hear with the hearing prosthesis. This can be achieved via the ability to receive raw answers to the tests from the recipient and/or via the abilities to receive scores of the tests given to the recipient. In this exemplary embodiment, the controller 1212 is a processor. The processor is configured to develop performance data based on the received input indicative of the recipient's ability to hear with the hearing prosthesis. In an exemplary embodiment, this performance data corresponds to one or more of the functions detailed above. In this embodiment, the processor is further configured to develop hypothetical efficacy data indicative of a subjective hypothetical efficacy of the hearing prosthesis based on the developed performance data (e.g. based on the function). In an exemplary embodiment, this developed hypothetical efficacy data are a forecast as detailed above. In an alternative embodiment, this developed hypothetical efficacy data are data indicative of what the efficacy would be if an alternate training scenario had been detailed.

In an exemplary embodiment, the processor 1212 is configured to develop hypothetical efficacy data indicative of the subjective hypothetical efficacy data of the hearing prosthesis based on hypothetical temporal data. In this regard, in an exemplary embodiment, the system is configured to receive data indicative of the hypothetical future training schedule of the recipient, and, based on this receive data, develop the hypothetical efficacy data. Accordingly, this hypothetical efficacy data are based on hypothetical temporal data, because the schedule inputted into the system is hypothetical, because it may not necessarily come to fruition.

In a similar vein, the processor is configured to develop hypothetical efficacy data indicative of the subjective hypothetical efficacy the hearing prosthesis based on data relating to a qualitative feature and/or a qualitative feature of hypothetical aural training tasks accomplished by the recipient. In this regard, in an exemplary embodiment, the system is configured to receive data indicative of hypothetical alternative training tasks, and based on this receive data, develop the hypothetical efficacy data.

As noted above, in at least some embodiments, the aural training tasks undertaken by the recipient may not be part of a given method in that they may be practice or otherwise executed outside of a given method. To account for this, in at least some embodiments, the system 1206 is configured to link data pertaining to aural training tasks undertaken by the recipient to respective aural tests of the plurality of aural tests provided to the recipient. The processor is configured to develop the aforementioned performance data based on the link data. This enables the system 1206 to manage the efficacy of the hearing prosthesis in relation to the aural training tasks based on the data indicative of the results of the aural tests.

As noted above, in at least some embodiments, at least some methods include providing the aural tests the recipient. Accordingly, in an exemplary embodiment, the system includes a device, such as by way of example only and not by way of limitation, the user interface 1214, that is configured to provide the recipient of the hearing prosthesis with a plurality of aural tests, the aural tests evoking respected hearing percepts with the hearing prosthesis. In some embodiments, this is achieved via a speaker or the like in the user interface 1214. In an alternative embodiment, this is achieved by a link 1208, which bypasses the microphones of the hearing prosthesis 100, and provides a direct signal to the hearing prosthesis. That said, in alternate embodiments, the system does not include this feature. In such exemplary embodiments, the system can be utilized in conjunction with another separate system that provides such tests. That said, in an alternate embodiment, the system can be utilized in conjunction with an audiologist that provide such tests.

In a similar vein, in at least some embodiments, the system 1206 is configured to provide the recipient with a plurality of temporally spaced aural training tasks that evoke a hearing percept. In this regard the user interface 1214 is configured to function in a manner similar to that just described with respect to the ability of the system to provide the tests.

Still further, as noted above, at least some embodiments of system 1206 have fitting functionalities. Accordingly, in an exemplary embodiment, the system 1206 is configured to execute a genetic algorithm to select a determined value set comprising values for a plurality of parameters of the hearing prosthesis. The genetic algorithm can be in accordance with that detailed above and/or variations thereof.

It is noted that the system 1206, detailed above, can execute one or more or all of the actions detailed herein and/or variations thereof automatically, at least those that do not require the actions of a recipient. It is noted that the schematic of FIG. 10 is functional. In some embodiments, a system 1206 is a self-contained device (e.g. a laptop computer, a so-called smart phone, etc.) that is configured to execute one or more or all of the method actions detailed herein and/or variations thereof, aside from those that utilize the recipient and/or the audiologist without receiving input from an outside source. In an alternative embodiment, system 1206 is a system having components located at various geographical locations. By way of example only and not by way of limitation, user interface 1214 can be located with the recipient, and the system controller (e.g., processor) 1212 can be located remote from the recipient. By way of example only and not by way of limitation, the system controller 1212 can communicate with the user interface 1214 via the Internet and/or via cellular communication technology or the like. Indeed, in at least some embodiments, the system controller 1212 can also communicate with the device 100 via the Internet and/or via cellular communication or the like. In an exemplary embodiment, the user interface 1214 can be a portable communications device, such as by way of example only and not by way of limitation, a cell phone and/or a so-called smart phone. Indeed, user interface 1214 can be utilized as part of a laptop computer or the like. Any arrangement that can enable system 1206 to be practiced and/or that can enable a system that can enable the teachings detailed herein and/or variations thereof to be practiced can be utilized in at least some embodiments.

Accordingly, an exemplary embodiment entails executing some or all of the method actions detailed herein where the recipient of the hearing prosthesis is located remotely (e.g., geographically distant) from where at least some of the method actions detailed herein are executed (e.g., any method action detailed herein that can be executed via the controller 1212). For example, the method of flowchart 200 could be executed via internet communication with the hearing prosthesis and the controller 1212. Still further by example, with respect to the method of flowchart 300, method action 310 can be executed at one location (controlled by the controller 1212 at another location geographically remote from the one location), and method action 320 could be executed at the location where controller 1212 is located, or at another location that is geographically remote from both locations). Indeed, in an exemplary embodiment, method action 310 can be executed at location A, method 320 can be executed at location B, and method 330 can be executed at location C. Location C could be, for example, the location of a remote server, where location A and location B are "connected" via the remote server. That is, any method action herein can be executed at one location, and any method action herein can be executed at another location, and so on, providing that the teachings detailed herein and/or variations thereof can be practiced.

It is further noted that in at least some embodiments, the system 1206 can enable the teachings detailed herein and/or variations thereof to be practiced at least without the direct participation of a clinician (e.g. an audiologist). Indeed, in at least some embodiments, the teachings detailed herein and/or variations thereof, at least some of them, can be practiced without the participation of a clinician entirely. In an alternate embodiment, the teachings detailed herein and/or variations thereof, at least some of them, can be practiced in such a manner that the clinician only interacts otherwise involves himself or herself in the process to verify that the results are acceptable or otherwise that desired actions were taken. In the above, it is noted that in at least some embodiments, a computerized automated application can be implemented to score or otherwise determine the results of the tasks detailed herein (e.g. listening task and/or memory task).

It is noted that any method detailed herein also corresponds to a disclosure of a device and/or system configured to execute one or more or all of the method actions associated there with detailed herein. In an exemplary embodiment, this device and/or system is configured to execute one or more or all of the method actions in an automated fashion. That said, in an alternate embodiment, the device and/or system is configured to execute one or more or all of the method actions after being prompted by the recipient and/or by the clinician.

Figure 11:
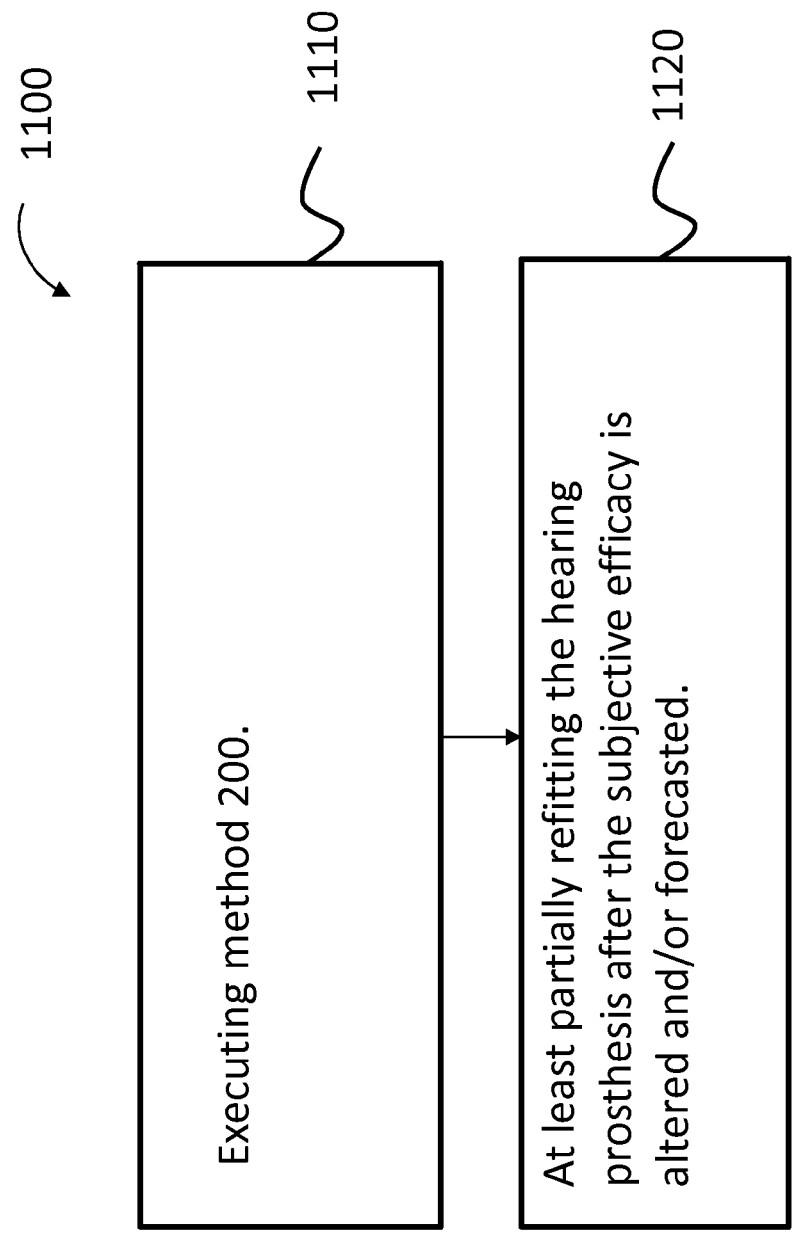
FIG. 11 presents another exemplary flowchart for an exemplary method according to an exemplary embodiment.

As noted above, some exemplary methods detailed herein include fitting (or at least partially fitting) a hearing prosthesis to a recipient. As detailed in method 200 of FIG. 2, the action of at least partially fitting the hearing prosthesis to the recipient occurs before the altering and/or forecasting the subjective efficacy the hearing prosthesis. That said, in some exemplary embodiments, there are some methods where the hearing prosthesis is refitted to the hearing prosthesis. In some exemplary embodiments, this can have utilitarian value in that the refitting process is executed after the efficacy of the hearing prosthesis has been improved relative to that which was the case when the hearing prosthesis was initially fitted to the recipient. In this vein, FIG. 11 presents an exemplary method 1100, which includes method action 1110, which entails executing method 200. Method 1100 further includes method action 1120, which entails at least partially refitting the hearing prosthesis after the subjective efficacy is altered and/or forecasted. In an exemplary embodiment, method 200 is executed, where the techniques detailed herein and/or variations thereof are practiced to alter the subjective efficacy of the hearing prosthesis.

By way of example only and not by way limitation, the techniques detailed herein are utilized to encourage the recipient to embark on a different training regime than that which was the case with respect to that of a prior time closer and temporal proximity to the initial fitting of the hearing prosthesis, thereby altering the subjective efficacy of the hearing prosthesis. After the subjective efficacy of the hearing prosthesis is altered according to these techniques, method action 1120 is executed. Still further by way of example only and not by way limitation, the techniques detailed herein are utilized to forecast a future subjective efficacy of the hearing prosthesis. At some later point, such as by way of example only and not by way of limitation, when the forecasted efficacy is achieved, method action 1120 is also executed. As with the action of at least partially fitting the hearing prosthesis of method 200, method action 1120 can be executed using any device, system and/or method of fitting a hearing prosthesis that can enable the teachings detailed herein and/or variations thereof to be practiced.

It is noted that any method detailed herein also corresponds to a disclosure of a device and/or system configured to execute one or more or all of the method actions associated there with detailed herein. In an exemplary embodiment, this device and/or system is configured to execute one or more or all of the method actions in an automated fashion. That said, in an alternate embodiment, the device and/or system is configured to execute one or more or all of the method actions after being prompted by the recipient and/or by the clinician.

It is noted that embodiments include non-transitory computer-readable media having recorded thereon, a computer program for executing one or more or any of the method actions detailed herein. Indeed, in an exemplary embodiment, there is a non-transitory computer-readable media having recorded thereon, a computer program for executing at least a portion of a method of evaluating subjective efficacy of a hearing prosthesis implanted in a recipient, the computer program including code for obtaining first data indicative of the recipient's ability to hear with the hearing prosthesis based on empirical data of performance by the recipient of temporally spaced aural tests that evoked a hearing percept with the hearing prosthesis, code for obtaining a function based on the first data, and code for obtaining second data indicative of the subjective efficacy of the hearing prosthesis based on the function.

In an exemplary embodiment, the media is such that the empirical data of performance is linked to temporal data pertaining to the temporally spaced aural tests and/or such that the empirical data of performance is linked to training type data. In an exemplary embodiment, the media is such that it further includes code for receiving recipient availability data indicative of future temporal periods in which the recipient will be able to participate in training with the hearing prosthesis, and code for developing a future training scenario based on the recipient availability data and based on the function. In an exemplary embodiment, the media is such that it further comprises code for obtaining future hearing prosthesis subjective efficacy target data, and code for developing a future training scenario based on the future hearing prosthesis subjective efficacy target data and the function.

In yet another exemplary embodiment, the media further includes code for obtaining recipient availability data indicative of temporal periods in which the recipient will be able to participate in training with the hearing prosthesis, code for obtaining future hearing prosthesis subjective efficacy target data, and code for developing a future training scenario based on the future hearing prosthesis subjective efficacy target data, the recipient availability data and the function. In an exemplary embodiment, the code for obtaining the second data includes code for obtaining the second data such that it is also indicative of a plurality of respective hypothetical efficacies of the hearing prosthesis based on the first data and based on respective alternate training scenarios. In an exemplary embodiment, the media comprises code for presenting a comparison between the plurality of hypothetical efficacies and/or code for recommending an alternate training scenario from the plurality of alternate training scenarios based on the comparisons of respective efficacies of the hearing prosthesis corresponding to respective alternate training scenarios of the plurality of alternate training scenarios.

Still further, in an exemplary embodiment, the media comprises code for providing the recipient with at least one of the aural tests or a plurality of temporally spaced aural training tasks that are respectively in close temporal proximity to respective tests of the tests.

It is noted that in an exemplary embodiment, there is a non-transitory computer-readable media having recorded thereon, a computer program for executing at least a portion of a method of evaluating subjective efficacy of a hearing prosthesis implanted in a recipient, the computer program including: code for obtaining first data indicative of the recipient's ability to hear with the hearing prosthesis based on empirical data of performance by the recipient of temporally spaced aural tests that evoked a hearing percept with the hearing prosthesis; code for obtaining a function based on the first data; and code for obtaining second data indicative of the subjective efficacy of the hearing prosthesis based on the function.

In an exemplary embodiment, there is the media as just described, wherein the empirical data of performance is linked to temporal data pertaining to the temporally spaced aural tests.

In an exemplary embodiment, there is the media as described above and/or below, wherein the empirical data of performance is linked to training type data.

In an exemplary embodiment, there is the media as described above and/or below, further comprising code for receiving recipient availability data indicative of future temporal periods in which the recipient will be able to participate in training with the hearing prosthesis; and code for developing a future training scenario based on the recipient availability data and based on the function.

In an exemplary embodiment, there is the media as described above and/or below, further comprising code for obtaining future hearing prosthesis subjective efficacy target data; and code for developing a future training scenario based on the future hearing prosthesis subjective efficacy target data and the function.

In an exemplary embodiment, there is the media as described above and/or below, further comprising code for obtaining recipient availability data indicative of temporal periods in which the recipient will be able to participate in training with the hearing prosthesis; code for obtaining future hearing prosthesis subjective efficacy target data; and code for developing a future training scenario based on the future hearing prosthesis subjective efficacy target data, the recipient availability data and the function.

In an exemplary embodiment, there is the media as described above and/or below, wherein the code for obtaining the second data includes code for: obtaining the second data such that it is also indicative of a plurality of respective hypothetical efficacies of the hearing prosthesis based on the first data and based on respective alternate training scenarios.

In an exemplary embodiment, there is the media as described above and/or below, further comprising code for presenting a comparison between the plurality of hypothetical efficacies.

In an exemplary embodiment, there is the media as described above and/or below, further comprising code for recommending an alternate training scenario from the plurality of alternate training scenarios based on the comparisons of respective efficacies of the hearing prosthesis corresponding to respective alternate training scenarios of the plurality of alternate training scenarios.

In an exemplary embodiment, there is the media as described above and/or below, further comprising code for providing the recipient with at least one of: the aural tests; or plurality of temporally spaced aural training tasks that are respectively in close temporal proximity to respective tests of the tests.

In an exemplary embodiment, there is the media as described above and/or below, further comprising code for at least partially fitting the hearing prosthesis to the recipient before obtaining the function.

In an exemplary embodiment, there is the media as described above and/or below, further comprising code for at least partially refitting the hearing prosthesis after obtaining the function and after the recipient has engaged in subsequent aural training tasks.

In an exemplary embodiment, there is a system for managing the subjective efficacy of a hearing prosthesis, comprising: a processor; and an input/output device configured to receive input indicative of the recipient's ability to hear with the hearing prosthesis, wherein the processor is configured to develop performance data based on the received input indicative of the recipient's ability to hear with the hearing prosthesis, and the processor is configured to develop hypothetical efficacy data indicative of a subjective hypothetical efficacy of the hearing prosthesis based on the developed performance data.

In an exemplary embodiment, there is a system as described above and/or below, wherein the system includes a device configured to provide a recipient of the hearing prosthesis with a plurality of aural tests, the aural tests evoking hearing percepts with the hearing prosthesis.

In an exemplary embodiment, there is a system as described above and/or below, wherein the processor is configured to develop hypothetical efficacy data indicative of the subjective hypothetical efficacy of the hearing prosthesis based on hypothetical temporal data.

In an exemplary embodiment, there is a system as described above and/or below, wherein: the processor is configured to develop hypothetical efficacy data indicative of the subjective hypothetical efficacy of the hearing prosthesis based on data relating to a qualitative feature and/or a quantitative feature of hypothetical aural tasks accomplished by the recipient.

In an exemplary embodiment, there is a system as described above and/or below, wherein the system is configured to link data pertaining to aural training tasks undertaken by the recipient to respective aural tests of the plurality of aural tests provided to the recipient; and the processor is configured to develop the performance data based on the linked data.

In an exemplary embodiment, there is a system as described above and/or below, wherein the system is configured to provide the recipient with a plurality of temporally spaced aural training tasks, the aural training tasks evoking hearing percepts evoked by the hearing prosthesis.

In an exemplary embodiment, there is a system as described above and/or below, further wherein the system is configured to provide the recipient with a plurality of temporally spaced aural training tasks, the aural training tasks evoking hearing percepts evoked by the hearing prosthesis; the system is configured to link data pertaining to respective temporally spaced aural training tasks of the plurality of temporally spaced aural training tasks to respective aural tests of the plurality of aural tests provided to the recipient; and the processor is configured to develop the performance data based on the linked data.

In an exemplary embodiment, there is a method of forecasting subjective efficacy of a hearing prosthesis implanted in a recipient, comprising subjecting a recipient to a plurality of temporally spaced aural tests, the aural tests evoking hearing percepts with the hearing prosthesis; obtaining first data indicative of the recipient's ability to hear with the hearing prosthesis based on performance by the recipient of the temporally spaced aural tests; and forecasting second data based on the first data, wherein the second data are indicative of the recipient's ability to hear with the hearing prosthesis at one or more temporal locations in the future.

In an exemplary embodiment, there is a method as described above and/or below, wherein: the first data are based on measurements of the ability of the recipient to hear with the hearing prosthesis taken in close temporal proximity to respective temporally spaced aural training tasks.

In an exemplary embodiment, there is a method as described above and/or below, wherein the first data are based on measurements of the ability of the recipient to hear with the hearing prosthesis taken in effective immediacy at least one of before or after respective temporally spaced aural training tasks.

In an exemplary embodiment, there is a method as described above and/or below, wherein: the first data are based on measurements of the ability of the recipient to hear with the hearing prosthesis taken at least one of before or after at least one of the aural training tasks without any cognitive stressors being located between the measurements and the respective aural training tasks.

In an exemplary embodiment, there is a method as described above and/or below, wherein: the first data are based on measurements of the ability of the recipient to hear with the hearing prosthesis taken before and after, both in close temporal proximity to, respective temporally spaced aural training tasks.

In an exemplary embodiment, there is a method as described above and/or below, further comprising: forecasting third data, wherein the third data are data indicating an estimated ability to hear with the prosthesis if temporally spaced aural training tasks are executed in the future with different temporal spacing between the tasks relative to that which was the case for temporally spaced aural training tasks temporally linked to respective temporally spaced aural tests of the plurality of temporally spaced aural tests.

In an exemplary embodiment, there is a method as described above and/or below, further comprising: comparing second data with the third data; and indicating to the recipient the effects of the different temporal spacing between the tasks relative to that which would be the case if temporally spaced aural training tasks are executed in the future with the same temporal spacing between the tasks relative to that which was the case for the temporally spaced aural training tasks temporally linked to the respective temporally spaced aural tests of the plurality of temporally spaced aural tests.

In an exemplary embodiment, there is a method as described above and/or below, further comprising: forecasting third data, wherein the third data are data indicating an estimated ability to hear with the prosthesis if temporally spaced aural training tasks are executed in the future that are different relative to that which was the case for tasks upon which the first data are based.

In an exemplary embodiment, there is a method as described above and/or below, further comprising: dynamically generating forecasts of data different than the second data, wherein the dynamically generated forecasted data are indicative of the recipient's ability to hear with the hearing prosthesis at one or more temporal locations in the future.

In an exemplary embodiment, there is a method as described above and/or below, further comprising: at least partially fitting the hearing prosthesis to the recipient before subjecting the recipient to the plurality of temporally spaced aural training tasks.

In an exemplary embodiment, there is a method as described above and/or below, further comprising: at least partially refitting the hearing prosthesis after forecasting the second data and after the recipient has engaged in subsequent aural training tasks.

In an exemplary embodiment, there is a method of altering a recipient's ability to hear with a hearing prosthesis implanted in a recipient, comprising: subjecting a recipient who has participated in a plurality of respective temporally spaced aural training tasks to a plurality of respective temporally spaced aural tests, the respective aural tests evoking hearing percepts evoked by the hearing prosthesis; and influencing the recipient's commitment to performing subsequent aural training tasks based on first data relating to the aural tests.

In an exemplary embodiment, there is a method as described above and/or below, further comprising: the action of influencing the recipient's commitment includes presenting second data to the recipient, the second data being indicative of negative repercussions to the recipient and being based on the first data.

In an exemplary embodiment, there is a method as described above and/or below, wherein the second data are data indicating the effects of temporal spacing between respective aural training tasks.

In an exemplary embodiment, there is a method as described above and/or below, wherein the second data are data indicating a difference in ability to hear with the prosthesis relative to that which would be the case if different temporal spacing between respective aural training tasks had occurred relative to that which was the case with respect to the participated aural training tasks.

In an exemplary embodiment, there is a method as described above and/or below, wherein the second data are data indicating a difference in ability to hear with the prosthesis relative to that which would be the case if shortened temporal spacing between respective aural training tasks had occurred.

In an exemplary embodiment, there is a method as described above and/or below, wherein the second data are data indicating a difference in ability to hear with the prosthesis relative to that which would be the case if additional aural training tasks had occurred.

In an exemplary embodiment, there is a method as described above and/or below, wherein the action of influencing the recipient's commitment includes presenting third data to the recipient, the third data being indicative of positive repercussions to the recipient.

In an exemplary embodiment, there is a method as described above and/or below, wherein the action of influencing the recipient's commitment includes presenting second data to the recipient, the second data being indicative of a forecasted ability to hear with the hearing prosthesis based on the first data.

In an exemplary embodiment, there is a method as described above and/or below, further comprising: at least partially fitting the hearing prosthesis to the recipient before subjecting the recipient to the plurality of temporally spaced aural tests.

In an exemplary embodiment, there is a method as described above and/or below, further comprising: at least partially refitting the hearing prosthesis after influencing the recipient's commitment to performing subsequent aural training tasks and after the recipient has engaged in the subsequent aural training tasks.

It is further noted that any device and/or system detailed herein also corresponds to a disclosure of a method of operating that device and/or using that device. Furthermore, any device and/or system detailed herein also corresponds to a disclosure of manufacturing or otherwise providing that device and/or system.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A method of forecasting subjective efficacy of a hearing prosthesis implanted in a recipient, comprising:
    subjecting a recipient to a plurality of temporally spaced aural tests, the aural tests evoking hearing percepts with the hearing prosthesis;
    obtaining first data indicative of the recipient's ability to hear with the hearing prosthesis based on performance by the recipient of the temporally spaced aural tests; and
    forecasting second data based on the first data, wherein the second data are indicative of the recipient's ability to hear with the hearing prosthesis at one or more temporal locations in the future.

2. The method of claim 1, wherein:
    the first data are based on measurements of the ability of the recipient to hear with the hearing prosthesis taken in effective immediacy at least one of before or after respective temporally spaced aural training tasks.

3. The method of claim 1, wherein:
    the first data are based on measurements of the ability of the recipient to hear with the hearing prosthesis taken at least one of before or after at least one of the aural training tasks without any cognitive stressors being located between the measurements and the respective aural training tasks.

4. The method of claim 1, wherein:
    the first data are based on measurements of the ability of the recipient to hear with the hearing prosthesis taken before and after, both in close temporal proximity to, respective temporally spaced aural training tasks.

5. The method of claim 1, further comprising
    forecasting third data, wherein the third data are data indicating an estimated ability to hear with the prosthesis if temporally spaced aural training tasks are executed in the future with different temporal spacing between the tasks relative to that which was the case for temporally spaced aural training tasks temporally linked to respective temporally spaced aural tests of the plurality of temporally spaced aural tests.

6. The method of claim 5, further comprising:
    comparing second data with the third data; and
    indicating to the recipient the effects of the different temporal spacing between the tasks relative to that which would be the case if temporally spaced aural training tasks are executed in the future with the same temporal spacing between the tasks relative to that which was the case for the temporally spaced aural training tasks temporally linked to the respective temporally spaced aural tests of the plurality of temporally spaced aural tests.

7. A method of altering a recipient's ability to hear with a hearing prosthesis implanted in a recipient, comprising:
    subjecting a recipient who has participated in a plurality of respective temporally spaced aural training tasks to a plurality of respective temporally spaced aural tests, the respective aural tests evoking hearing percepts evoked by the hearing prosthesis;
    influencing the recipient's commitment to performing subsequent aural training tasks based on first data relating to the aural tests; and
    at least partially refitting the hearing prosthesis after influencing the recipient's commitment to performing subsequent aural training tasks and after the recipient has engaged in the subsequent aural training tasks.

8. The method of claim 7, wherein:
    the action of influencing the recipient's commitment includes presenting second data to the recipient, the second data being indicative of negative repercussions to the recipient and being based on the first data.

9. The method of claim 8, wherein:
    the second data are data indicating the effects of temporal spacing between respective aural training tasks.

10. The method of claim 8, wherein:
    the second data are data indicating a difference in ability to hear with the prosthesis relative to that which would be the case if different temporal spacing between respective aural training tasks had occurred relative to that which was the case with respect to the participated aural training tasks.

11. The method of claim 8, wherein:
    the second data are data indicating a difference in ability to hear with the prosthesis relative to that which would be the case if additional aural training tasks had occurred.

12. The method of claim 7, further comprising:
    at least partially fitting the hearing prosthesis to the recipient before subjecting the recipient to the plurality of temporally spaced aural tests.

13. A system for managing the subjective efficacy of a hearing prosthesis, comprising:
    a processor; and
    an input/output device configured to receive input indicative of the recipient's ability to hear with the hearing prosthesis, wherein
    the processor is configured to develop performance data based on the received input indicative of the recipient's ability to hear with the hearing prosthesis,
    the processor is configured to develop hypothetical efficacy data indicative of a subjective hypothetical efficacy of the hearing prosthesis based on the developed performance data, and
    the processor is configured to develop hypothetical efficacy data indicative of the subjective hypothetical efficacy of the hearing prosthesis based on hypothetical temporal data.

14. The system of claim 13, wherein:
    the system includes a device configured to provide a recipient of the hearing prosthesis with a plurality of aural tests, the aural tests evoking hearing percepts with the hearing prosthesis.

15. The system of claim 13, wherein:
    the processor is also configured to develop additional hypothetical efficacy data indicative of the subjective hypothetical efficacy of the hearing prosthesis based on data relating to a qualitative feature and/or a quantitative feature of hypothetical aural tasks accomplished by the recipient.

16. The system of claim 13, wherein:
    the system is configured to link data pertaining to aural training tasks undertaken by the recipient to respective aural tests of the plurality of aural tests provided to the recipient; and
    the processor is configured to develop the performance data based on the linked data.

17. The system of claim 13, wherein:
    the system is configured to provide the recipient with a plurality of temporally spaced aural training tasks, the aural training tasks evoking hearing percepts evoked by the hearing prosthesis;
    the system is configured to link data pertaining to respective temporally spaced aural training tasks of the plurality of temporally spaced aural training tasks to respective aural tests of the plurality of aural tests provided to the recipient; and the processor is configured to develop the performance data based on the linked data.

18. The method of claim 1, further comprising:

adjusting a structural and/or functional feature of the hearing prosthesis, thereby tailoring and/or customizing the hearing prosthesis.

19. The method of claim 7, wherein the action of influencing the recipient's commitment includes presenting second data to the recipient, the second data being indicative of a forecasted ability to hear with the hearing prosthesis based on the first data.

20. The method of claim 7, wherein:

the action of influencing the recipient's commitment includes presenting second data to the recipient, wherein the second data are data indicating the effects of temporal spacing between respective aural training tasks.

21. The method of claim 7, wherein:

the action of influencing the recipient's commitment includes presenting second data to the recipient, wherein the second data are data indicating a difference in ability to hear with the prosthesis relative to that which would be the case if different temporal spacing between respective aural training tasks had occurred relative to that which was the case with respect to the participated aural training tasks.

22. The system of claim 13, wherein:

the system is further configured to identify how to change an efficacy of the prosthesis.

* * * * *